United States Patent
Kinsella et al.

(10) Patent No.: US 11,111,305 B2
(45) Date of Patent: Sep. 7, 2021

(54) METHOD OF USING A BISPECIFIC ANTIBODY TO CONDITIONALLY INHIBIT A RECEPTOR SIGNALING COMPLEX

(71) Applicant: TORCH THERAPEUTICS, Hillsborough, CA (US)

(72) Inventors: Todd M. Kinsella, Redwood City, CA (US); Donald G. Payan, Hillsborough, CA (US); Ramesh Bhatt, Belmont, CA (US); Kristen Baltgalvis, Poway, CA (US)

(73) Assignee: TORCH THERAPEUTICS, Hillsborough, CA (US)

( * ) Notice: Subject to any disclaimer, the term of this patent is extended or adjusted under 35 U.S.C. 154(b) by 0 days.

(21) Appl. No.: 16/475,342

(22) PCT Filed: Jan. 9, 2018

(86) PCT No.: PCT/US2018/012948
§ 371 (c)(1),
(2) Date: Jul. 1, 2019

(87) PCT Pub. No.: WO2018/129522
PCT Pub. Date: Jul. 12, 2018

(65) Prior Publication Data
US 2019/0345252 A1    Nov. 14, 2019

Related U.S. Application Data

(60) Provisional application No. 62/581,224, filed on Nov. 3, 2017, provisional application No. 62/444,266, filed on Jan. 9, 2017, provisional application No. 62/444,257, filed on Jan. 9, 2017.

(51) Int. Cl.
*C07K 16/28* (2006.01)
(52) U.S. Cl.
CPC ........ *C07K 16/2863* (2013.01); *C07K 16/289* (2013.01); *C07K 2317/31* (2013.01); *C07K 2317/73* (2013.01); *C07K 2317/76* (2013.01)

(58) Field of Classification Search
CPC .. C07K 16/00; C07K 16/2863; C07K 16/289; C07K 2317/31; C07K 2317/70; C07K 2317/73; C07K 2317/76; A61K 2039/505
See application file for complete search history.

(56) References Cited

U.S. PATENT DOCUMENTS

| | | |
|---|---|---|
| 3,773,919 A | 11/1973 | Boswell |
| 7,612,181 B2 | 11/2009 | Wu et al. |
| 8,216,805 B2 | 7/2012 | Carter et al. |
| 9,358,286 B2 | 6/2016 | De Kruif et al. |
| 2012/0149876 A1 | 7/2012 | Von Kreudenstein et al. |
| 2014/0288275 A1 | 9/2014 | Moore et al. |

FOREIGN PATENT DOCUMENTS

| | | |
|---|---|---|
| WO | WO 2012/058768 | 5/2012 |
| WO | WO 2013/063702 | 5/2013 |
| WO | WO 2014/110601 | 7/2014 |
| WO | WO 2014/145806 | 9/2014 |

OTHER PUBLICATIONS

Anderson et al., 2004, Proc Natl Acad Sci USA 101 (2):7566-71.
Atwell et al., J. Mol. Biol. 1997 270:26.
Avin et al., The Journal of Immunology, 173(7), 2004.
Chin et al., 2003, Science 301(5635):964-7.
Cropp & Shultz, 2004, Trends Genet. 20(12):625-30.
Efimov et al., PNAS, 113(11), 2016.
Kashio et al., J Biol Chem. Dec. 11, 1998;273(50):33856-63.
Kontermann, mAbs 4:2, 182-197, 2012.
Kuban-Jankowska et al., PLOS ONE Journal, 7(12), 2012.
Ridgway et al., Protein Engineering 9(7):617, 1996.
Spiess et al., Mol. Immunol, 2015.
Zhang et al., 2003, 303(5656):371-3.

*Primary Examiner* — Robert S Landsman
(74) *Attorney, Agent, or Firm* — Morgan, Lewis & Bockius LLP; Christina A. MacDougall

(57) ABSTRACT

This invention describes the design of bispecific antibodies that function as conditionally effective therapeutics by binding to a functionally silent epitope on one component of a targeted signaling complex and simultaneously binding to a second protein, whose expression or accessibility is cell- or disease environment-specific, and whose antibody-driven proximity to the signaling complex leads to an alteration of signal transduction.

1 Claim, 15 Drawing Sheets

Applications of Zip Coding Bispecific Technology

| Receptor target | Zip Code target | Indication | Clinical / mechanistic advantage |
|---|---|---|---|
| TGFBR2 | CD45<br>*Cell selectivity*<br>*Immune cells* | Immuno-oncology (TGFβ-driven immunosuppression) | Selectively target immune cells while avoiding cardiovacular & other pleiotropic toxicities; Permit maximal inhibition |
| TGFBR2 | FAP<br>*Activated stromal fibroblasts*<br>*(> 90% cancers)* | Immuno-oncology (TGFβ-driven immunosuppression & activation), Fibrosis associated with chronic liver disease, Idiopathic Pulmonary Fibrosis | Selectively target activated stromal fribroblasts while avoiding cardiovacular & other pleiotropic toxicities; Permit maximal inhibition |
| GMCSFRa (CSF2RA) | FAP<br>MDSC | Immuno-oncology (MDSC activation & proliferation) | Selectively inhibit GM-CSF signaling in MDSCs while avoid counterproductive inhibition of GM-CSF signaling in other key immune cells (i.e. DC) |
| SIRPa | PD-L1<br>*Expression on tumor associated macrophages* | Immuno-oncology (CD47-driven immune escape) | Selectively target tumor infiltrated macrophages while avoiding dose-dependent anemia |
| IL2R | PD-L1<br>*Tumor infiltrating Tregs* | Immuno-oncology (Tumor-selective reduction of Treg function) | Selectively target tumor infiltrated Tregs while avoiding counterproductive inhibition of IL-2 signaling in other key immune cells (i.e. CD8 T cells) (limit immune-related adverse events) |
| PD-1 | KCNMA1, others<br>*Exhausted tumor infiltrating lymphocytes* | Immuno-oncology (Tumor-selective reinvigoration of CD8 T cells) | Selectively target tumor infiltrated T cells while avoiding healthy organ resident lymphocytes (limit immune-related adverse events) |

*FIG. 6*

METHOD OF USING A BISPECIFIC ANTIBODY TO CONDITIONALLY INHIBIT A RECEPTOR SIGNALING COMPLEX

I. CROSS REFERENCE TO RELATED APPLICATIONS

This application claims priority to U.S. Provisional Application No. 62/444,257 filed on Jan. 9, 2017, U.S. Provisional Application No. 62/444,266 filed Jan. 9, 2017, and U.S. Provisional Application No. 62/581,224 filed Nov. 3, 2017, all of which are expressly incorporated by reference in their entireties.

II. BRIEF SUMMARY OF THE INVENTION

Cell surface mediated protein signaling generally involves the binding of at least two different molecules, in cis or in trans, to initiate signal transduction. This initial binding event can be binary (a single ligand and receptor) but most often involves the assembly of multi-component complexes into higher order structures that serve as the triggering event for signal initiation. The ability of ligands and receptors to productively bind and assemble into complexes requires that the interacting surfaces of each protein be sterically accessible in order to allow for prerequisite surface matching and non-covalent interaction formation. These signaling events are regulated by structural motifs found in hormone receptors, cytokine receptors, etc where one of the members of the receptor is a common chain having activity across multiple signaling systems (ie, gp 130). Further, the successful assembly of binary or multimeric signaling complexes requires sufficient amounts of open space around the binding sites to accommodate the full volume of the assembled signaling proteins. Thus, a zone of open space around each component, which encompasses the interacting surfaces and the volume of the fully assembled complex, is a requirement for successful initiation of signal transduction.

Carefully designed bispecific antibodies can function as conditionally active therapeutics whose activity is uncovered by the tissue selective function of one of the receptor components by binding to a functionally silent epitope on one component of the signaling complex and simultaneously projecting a second protein, whose expression is cell- or disease environment-specific, into the zone of open space normally occupied by the ligand and/or other receptor components during signaling complex formation. Thus, steric inhibition of the receptor signaling complex becomes conditionally dependent upon the expression and function of the second protein targeted by the bispecific antibody, hereby referred to as the "ZipCode" protein. Using these design principles, bispecifics can be created to selectively modify receptor signaling in specific cell types, tissues or disease environments that induce the expression of the ZipCode protein. Since the other complementary determining region (CDR) of the bispecific has been designed to bind to a functionally silent epitope of the targeted receptor signaling complex, it is by definition, incapable of inhibiting signal transduction in the absence of the ZipCode protein, and would therefore be expected to be inactive in cells lacking sufficient expression of the ZipCode protein, or in tissues where the zip coded protein's proximity to the target of interest is not facilitated by activation constraints (ie, moving into an immunological synapse).

Cell- and/or tissue-selective inhibition of signaling can have many advantages, most notably as a way to avoid unwanted toxicities that can arise when cells expressing the targeted receptors have important physiological roles outside of the intended therapeutic effect in a specific tissue. For example, selectively targeting the type II receptor for TGFβ, TGFBR2, in immune cells while avoiding inhibition in cardiac tissues might eliminate the hemorrhagic & degenerative heart valve lesions associated with inhibitors of TGFβ signaling. This might be accomplished by adhering to the design principles outlined in this invention and pairing bispecific binding of TGBR2 with CD45, which is selectively expressed on immune cells. The antibody binds to a functionally silent epitope on the TGFBR that is in spatial proximity to the active ligand binding site on the receptor, but whose engagement by the antibody elicits no functional event that is TGFB related. The "proximity trapping" of CD45 by the antibody and bringing it into proximity of TGFβ signaling essentially results in the antibody positioning CD45 as a receptor blocker that is immune tissue selective. Other examples include pairing the binding of PD-1 with ZipCode proteins that are robustly induced on immune cells exposed to the tumor microenvironment, such as KCNMA1, for selective inhibition of PD-1 signaling in tumor infiltrating lymphocytes and avoidance of autoimmunity in heathy organ tissue.

The selectivity afforded by the conditionally active bispecifics outlined here has the potential to avoid certain on-target toxicities being wide spread into tissues otherwise not intended for inhibition/activation, as in the case of TGFB inhibition in cardiac tissue during efforts to reactivate the immune response in the tumor microenviroment by limiting the inhibition to specific cell types or disease environments (i.e only cells exposed to conditions present in a diseased tissue capable of up regulating the "ZipCode" protein and thereby triggering the conditional activity). Other examples include the regulation of immune cell types that are altered in the tumor microenvironment resulting in diminished removal of the tumor. It is these tumor resident immune cells that one wants to turn on and activate as a way to remove tumor tissue. These cells have upregulated cell surface receptors (they in fact are responsible for the check point nature of the immune inhibition by tumor factors) that can serve as Zip coded targets, since the goal is to not regulate these immune cells in the non tumor environment, thus mitigating autoimmune responses that cause severe systemic toxicities. Zip coded targets need to be identified by their tissue selective nature and by the fact that they get induced in a functionally selective/disease relevant manner, thus one can use the bispecific nature of the therapy to direct a therapeutic antibody to the target of regulatory/medical interest and the zip coded protein endows the therapy with tissue selectivity. A major benefit of this new approach will enable higher doses to be delivered without off tissue toxicities and specially to minimize systemic auto immune responses leading to excessive morbidity and mortality with combined immune oncology therapeutics.

III. BRIEF DESCRIPTION OF THE DRAWINGS

Pathol. 2011; 39:916-924 and Stauber et al., Society of Toxicology, 45th Annual Meeting and Tox Expo, 2006 (abstr 290).

Figure 3:
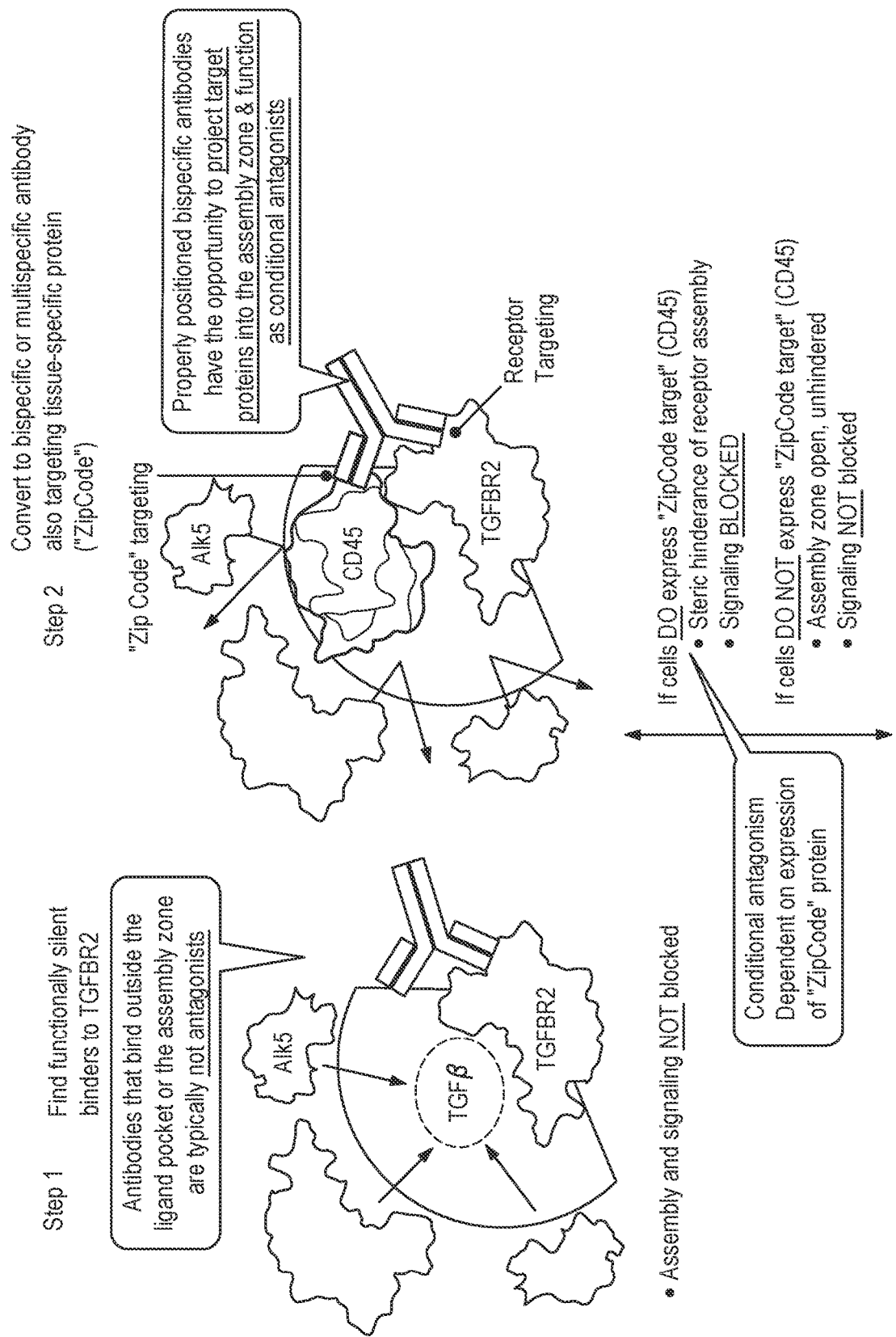

FIG. 3 shows the general mechanism of the conditional antagonist mechanism of the BCEs of the invention.

Figure 4:
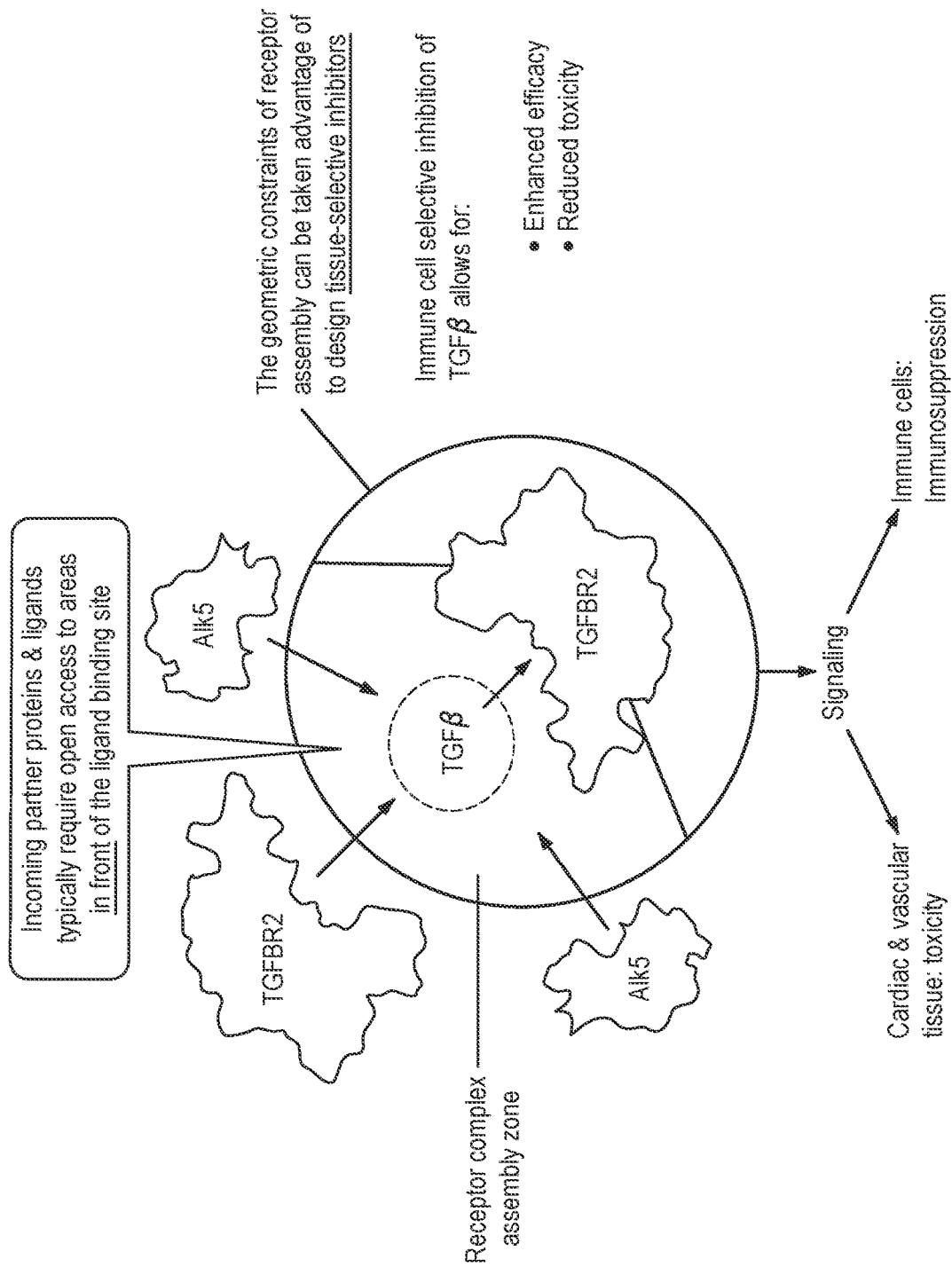

FIG. 4 shows the general mechanism of the invention.

Figure 5:
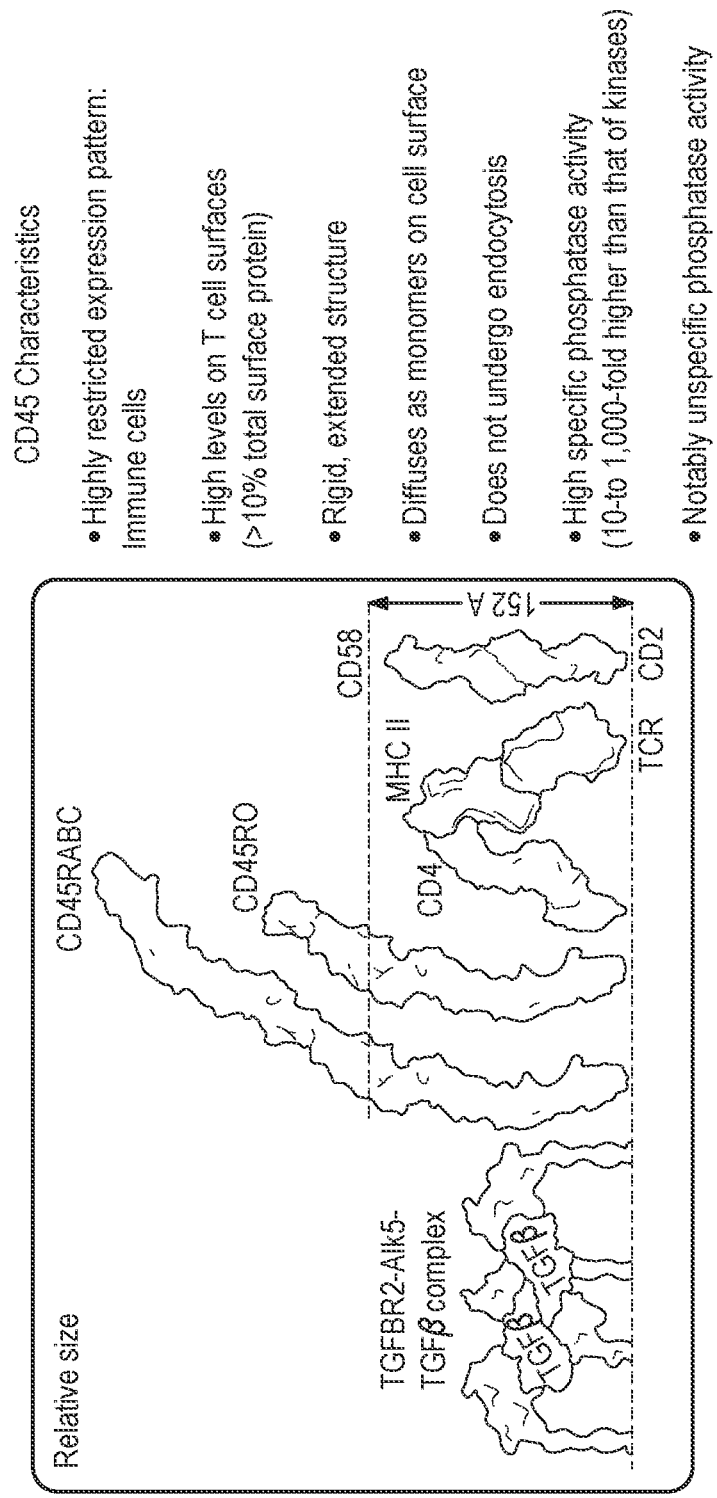

FIG. 5 shows the desirable features of CD45 as a target "zipcode" protein.

FIG. 6 shows some preferred embodiments for the combinations of receptor proteins and target proteins.

Figure 7B:
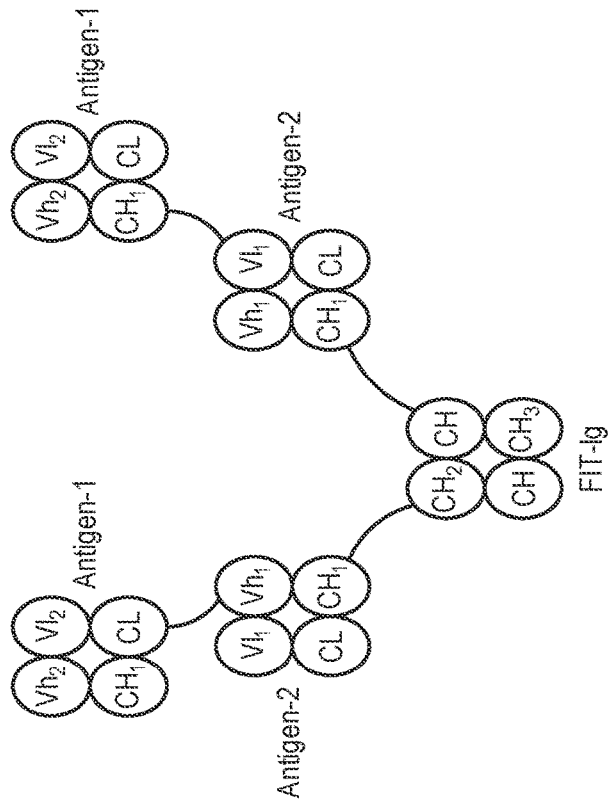
Figure 7D:
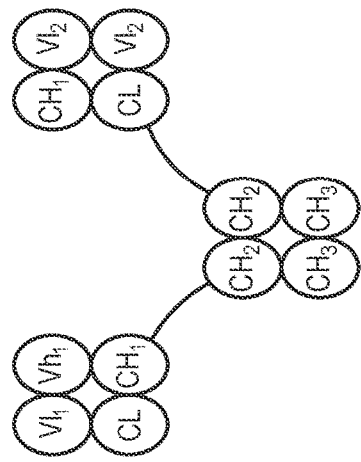
Figure 7A:
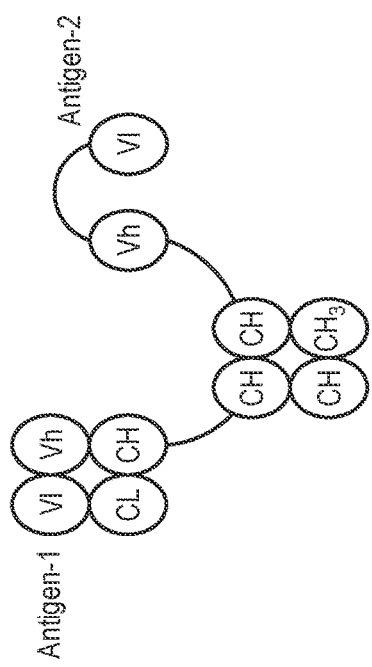
Figure 7C:
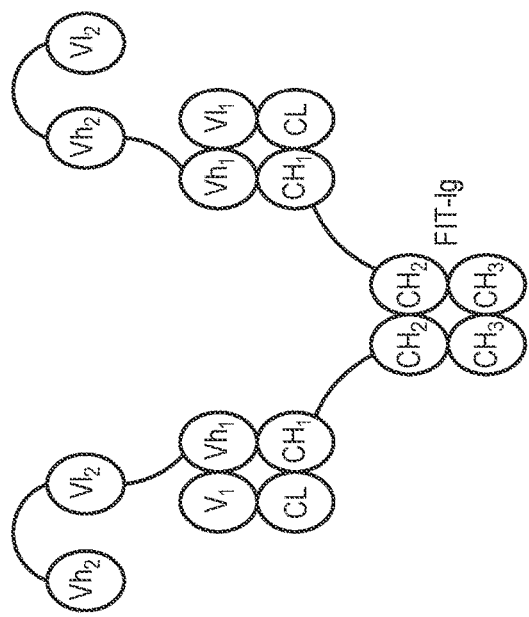

FIG. 7A-FIG. 7D depicts a number of different known bispecific formats that find use in the present invention. FIG. 7A is a scFv-Fab heterodimeric bispecific bivalent format, FIG. 7B is a "Fabs in Tandem" ("FIT-Ig") homodimeric bispecific, tetravalent format, FIG. 7C is a DVD-Ig homodimeric bispecific, tetravalent format, and FIG. 7D is a heterodimeric Fab format.

Figure 8A:
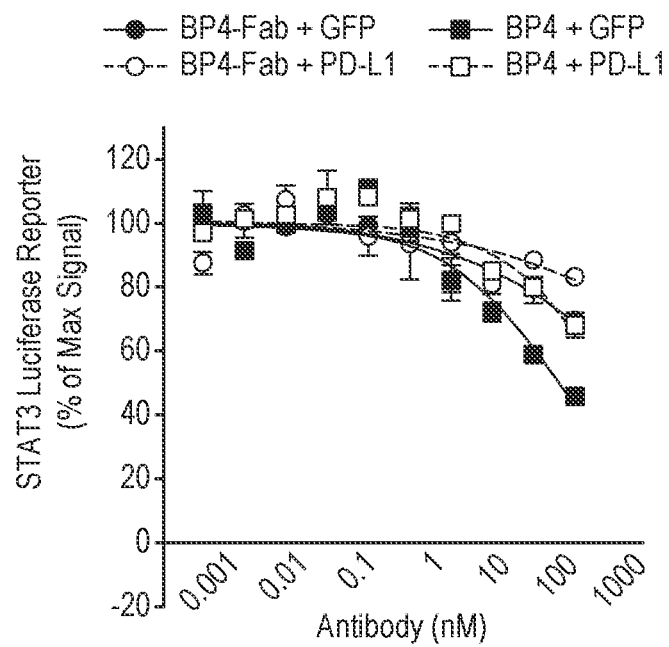
Figure 8B:
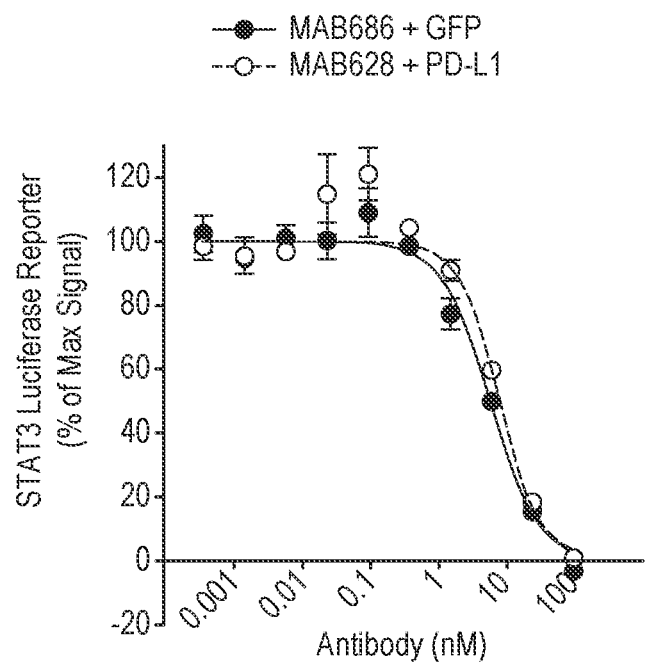

FIG. 8A-FIG. 8C shows the effect of various antibodies on cells expressing PD-L1, the "zipcode" in this system (solid line) or not (dashed line). Panel A shows that a bispecific gp130×PD-L1 antibody (in an scFv-Fab format as depicted in FIG. 7A) shows selective and potent inhibition on PD-L1 bearing cells. Cells treated with conventional gp130 antibodies potently inhibit irrespective of the presence or absence of the Zipcode PD-L1 (panel B). Panel C shows the lack of effect of a non-inhibitory gp130 mAb. This was done using the scFv-Fab heterodimeric format with "knobs-in-holes" variants.

Figure 9:
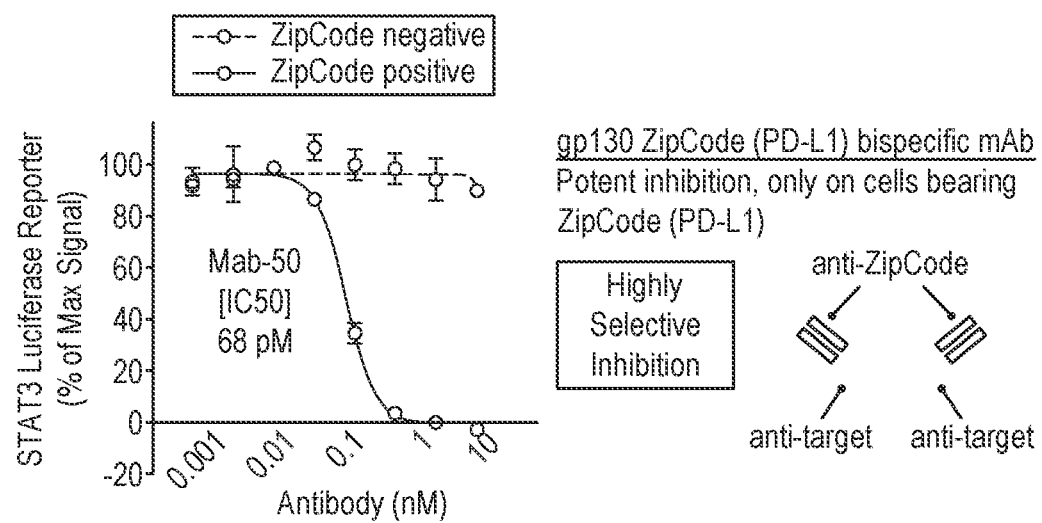

FIG. 9 shows the effect of a bispecific, tetravalent antibody on cells expressing PD-L1, the "zipcode" in this system (solid line) or not (dashed line), this time using a bispecific tetravalent "FIT-Ig" construct (as depicted in FIG. 7B). The tetravalent construct potently and selectively inhibited PD-L1 ZipCode producing cells than wild type cells.

Figure 10A:
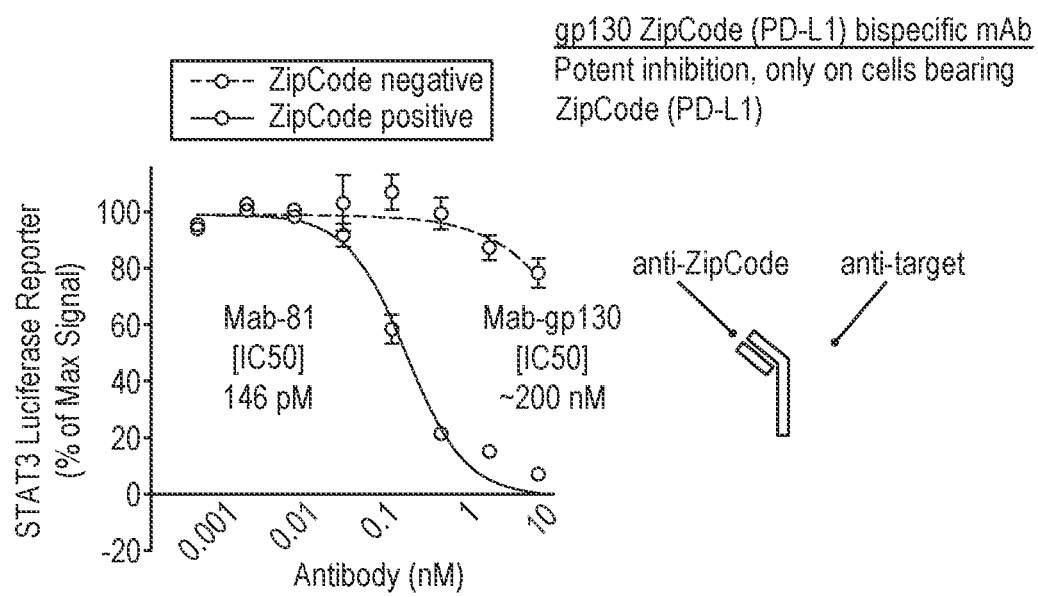
Figure 10B:
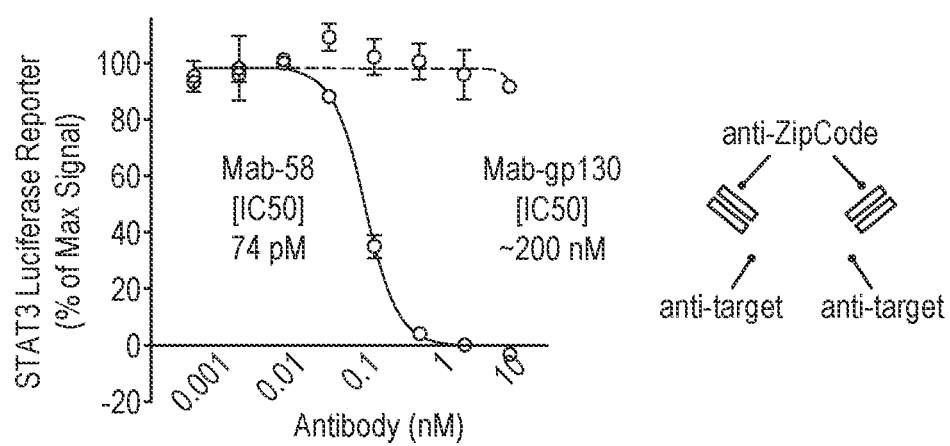

FIG. 10A-FIG. 10B shows the effect of the Fc backbone (e.g. IgG1 and IgG2) on the bivalent and tetravalent bispecific constructs as above. In FIG. 10A, the Mab-gp130 is the IgG1 backbone and Mab-81 is the IgG2 backbone. FIG. 10B the Mab-58 is the tetravalent bispecific format in IgG2.

Figure 11A:
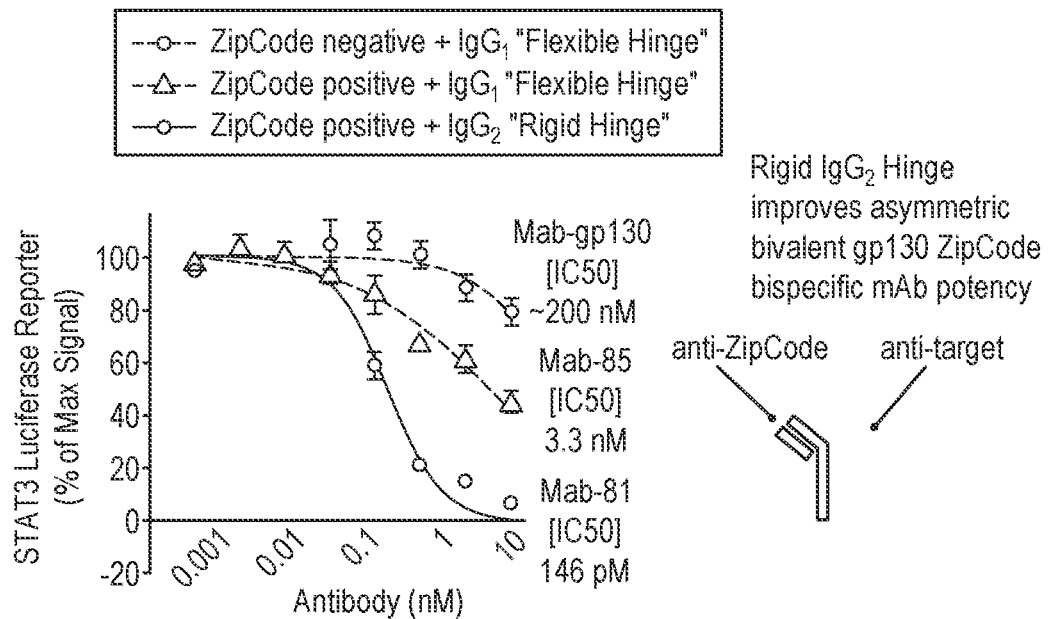
Figure 11B:
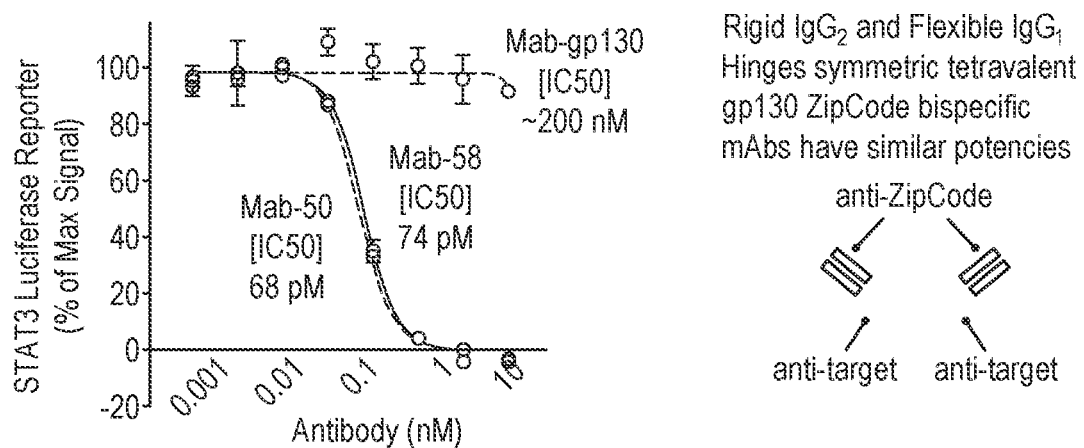

FIG. 11A-FIG. 11B evaluates the differences in the rigidity of the hinge regions used in the constructs. In this case, the bivalent bispecific IgG1 Mab-81 contains a "rigid" linker, e.g. the hinge from IgG2, the bivalent, bispecific Mab-85 contains a more "flexible" linker, e.g. the hinge from IgG1, the tetravalent, bispecific Mab-50 has the "flexible" IgG1 hinge and the tetravalent, bispecific Mab-58 has the more "rigid" IgG2 hingeInterestingly, the rigid linker improves activity in the bivalent format while the tetravalent format showed no substantial alteration.

Figure 12A:
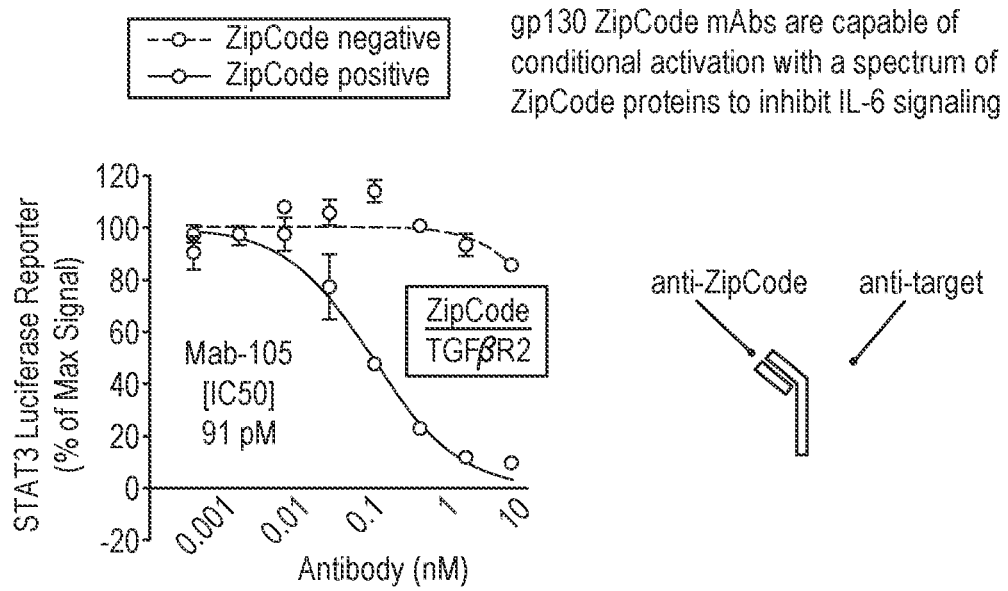
Figure 12B:
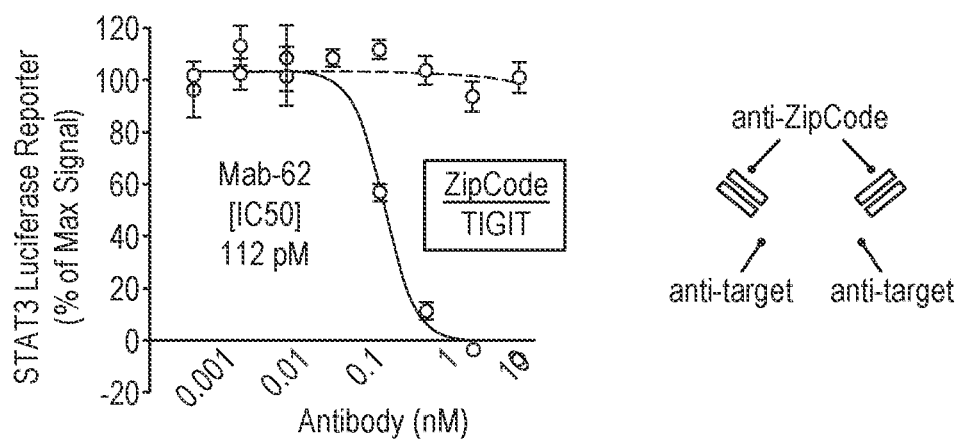

FIG. 12A-FIG. 12B show similar activities using different Zipcode antigens, TGFβR2 and TIGIT (a different checkpoint inhibitor). FIG. 12A shows the effect of a bivalent bispecific format and FIG. 12B shows the tetravalent bispecific format.

Figure 13:
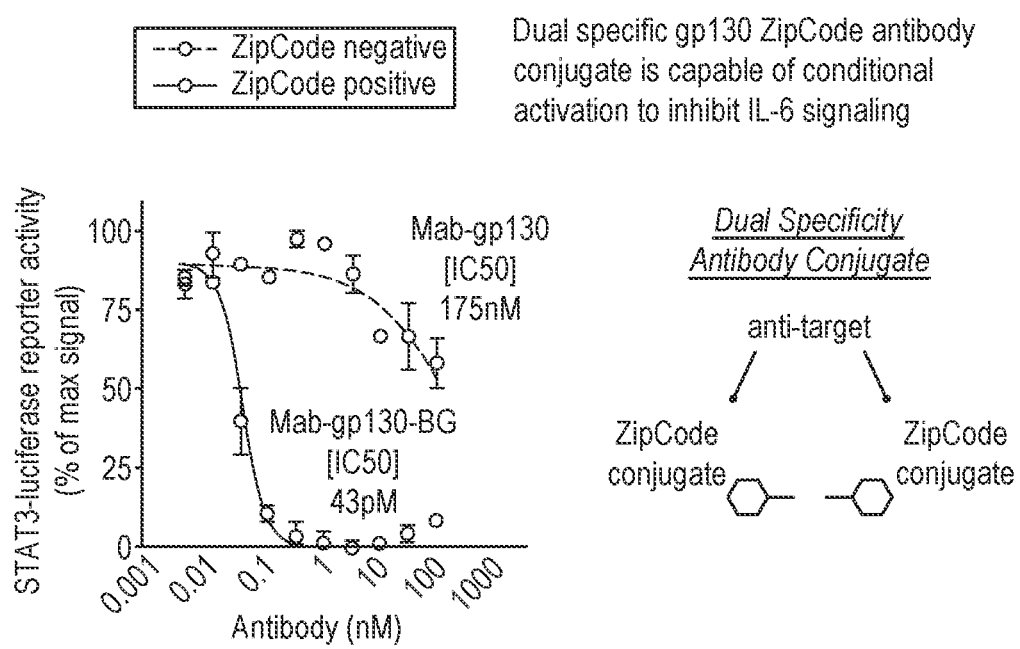
Figure 14A:
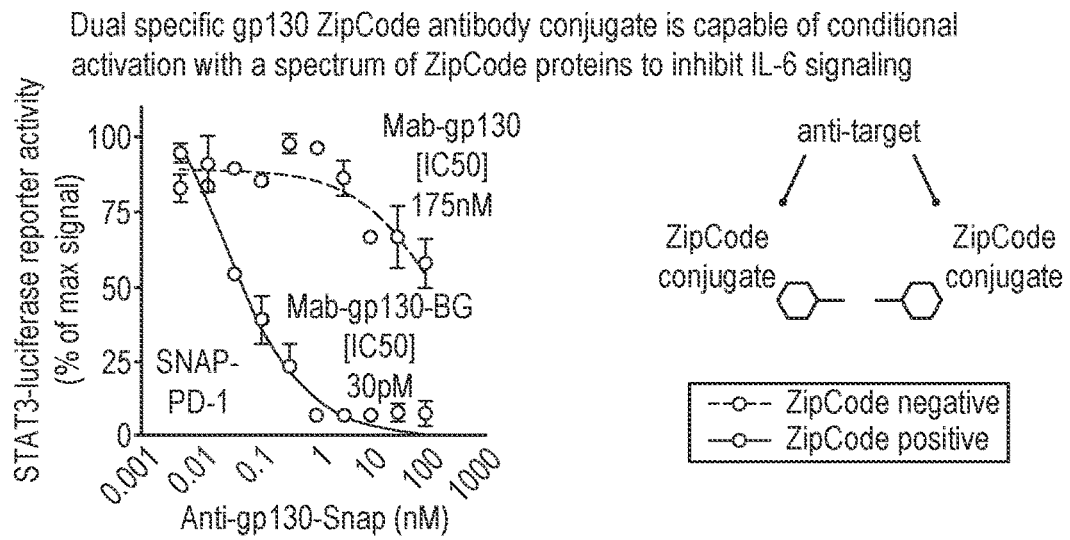
Figure 14B:
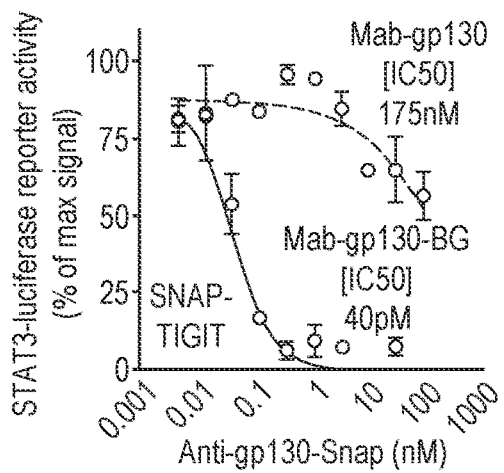
Figure 14C:
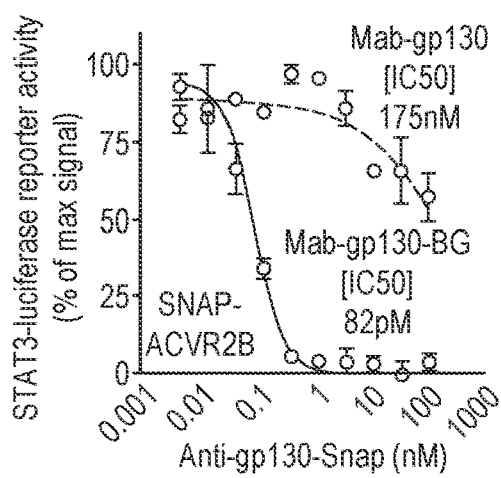
Figure 14D:
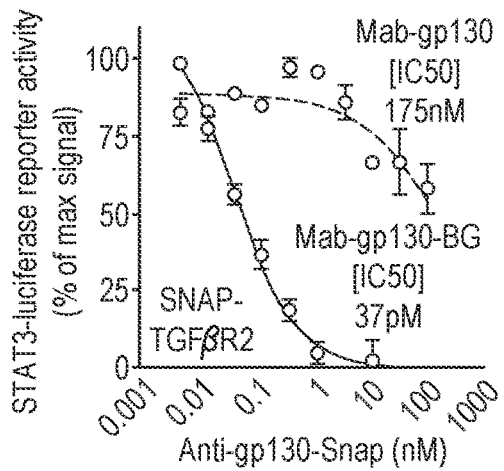
Figure 14E:
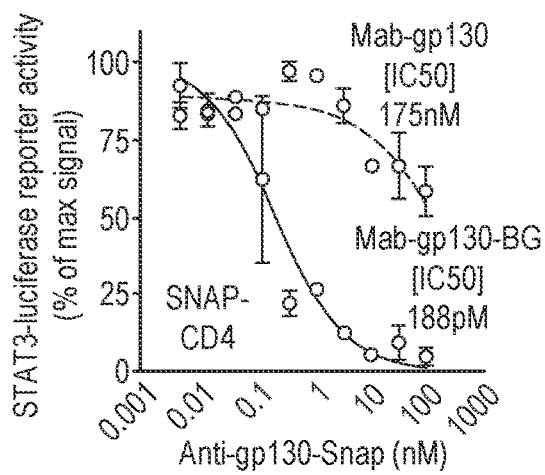

FIG. 13 depicts the fact that the conditional activation is not limited to the use of protein-protein interactions, it can be used with other moieties that sterically interfere. As described in Example 6, the use of a SNAP tag that binds PD-1 (in this case, PD-L1 is used as the conjugate).

FIG. 14A-FIG. 14E show that the antibody conjugate technology described in FIG. 13 can be similarly applied to a number of different cell surface receptors, including PD-1, TIGIT, ACVR2B, TGFβR2 and CD4.

Figure 15:
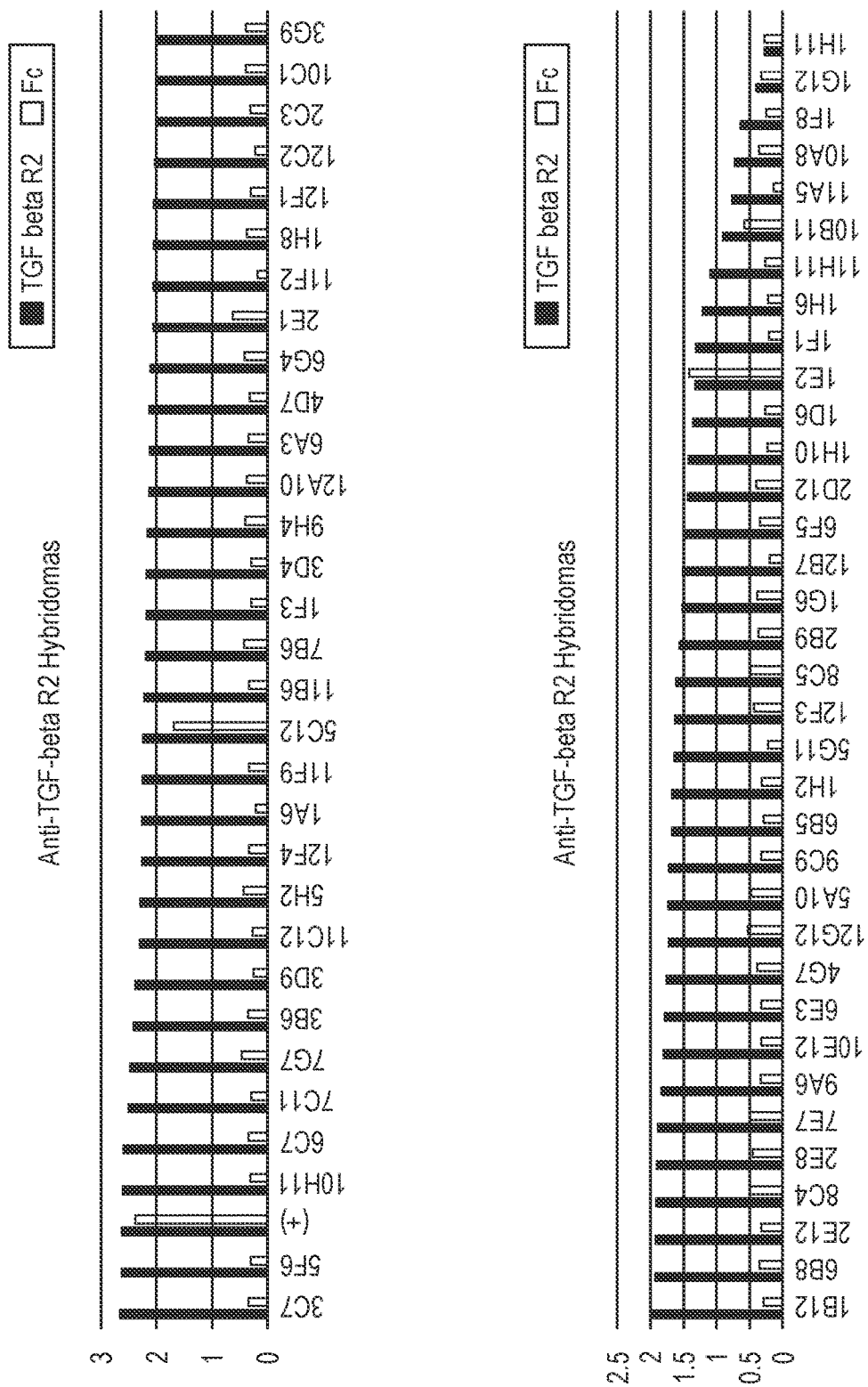

FIG. 15 shows the hybridoma ELISA data from Example 8.

IV. DETAILED DESCRIPTION OF THE INVENTION

A. Definitions

By "receptor protein" or "receptor complex protein" herein is meant a protein of a signal transduction complex of proteins. Signal transduction is the process by which a chemical or physical signal is transmitted through a cell as a series of molecular events, most commonly protein phosphorylation, which ultimately result in a response. Proteins responsible for detecting stimuli, such as ligands, are generally termed "receptors" or "receptor proteins". The changes elicited by ligand binding in a receptor give rise to a cascade of biochemical events along a signaling pathway. At the molecular level, such responses include changes in the transcription or translation of genes, and post-translational and conformational changes in proteins, as well as changes in their location. These molecular events are the basic mechanisms controlling cell growth, proliferation, metabolism and many other processes. Each protein of a signaling pathway is classified according to the role it plays with respect to the initial stimulus. Ligands are termed first messengers, while receptors are the signal transducers, which then activate primary effectors. Examples of receptor proteins suitable for use in the present invention are described more fully below. In general, for the purposes of the invention, receptor complexes have at least two components, a ligand and a receptor protein that binds the ligand in the active site of the receptor protein; in some embodiments, the receptor complex can include additional receptor complex proteins (such as primary effector proteins).

By "target protein" or "zipcode protein" herein is meant a protein that is expressed on a particular cell that is involved in a disease state of interest. Examples of suitable zipcode proteins for use in the present invention are described more fully below.

By "ligand" herein is meant a signaling molecule that binds to the active site of a receptor protein to effect signaling. The ligand molecule may be a protein (including, but not limited to, cytokines and growth hormones), neurotransmitters, steroid hormones, small molecules, etc.

By "active site" herein is meant the location on a receptor protein to which a ligand binds. As discussed herein, the invention is directed to bispecific antibodies with an antigen binding domain (ABD) that is "outside" the active site of the receptor protein, e.g. at an epitope that does not prevent the binding of the ligand to the receptor. The lack of binding and/or blocking the active site can be done in a variety of ways, as will be appreciated by those in the art. For example, Biacore® type assays can be done to test whether the antibody containing the Fv that binds to the receptor protein prevents its cognate ligand binding; alternatively, functional biochemical assays can be done to measure the effect of ligand binding on the receptor protein in the presence of the antibody, as will be appreciated by those in the art. In other embodiments, the disruption of receptor oligomerization due to the presence of the ZipCode can be measured using known techniques.

By "antigen binding domain" or "ABD" herein is meant a set of six Complementary Determining Regions (CDRs) that, when present as part of a polypeptide sequence, specifically binds a target checkpoint antigen as discussed herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3, vlCDR1, vlCDR2 and vlCDR3. The CDRs are present in the variable heavy and variable light domains, respectively, and together form an Fv region. In a "Fab" format, the set of 6 CDRs are contributed by two different polypeptide sequences, the variable heavy domain (vh or $V_H$; containing the vhCDR1, vhCDR2 and vhCDR3) and the variable light domain (vl or $V_L$; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker as outlined herein, into a single polypeptide sequence, which can be either (starting from the N-terminus) vh-linker-vl or vl-linker-vh.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233# or E233( ) designates a deletion of glutamic acid at position 233. Additionally, EDA233- or EDA233# designates a deletion of the sequence GluAspAla that begins at position 233.

By "variant protein" or "protein variant", or "variant" as used herein is meant a protein that differs from that of a parent protein (e.g. a wild type human protein) by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as M428L/N434S, and so on. For all positions discussed in the present invention that relate to antibodies, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homophenylalanine, citrulline, ornithine and norleucine are considered synthetic amino acids for the purposes of the invention, and both D- and L-(R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "Fab" or "Fab region" as used herein is meant the polypeptide that comprises the VH, CH1, VL, and CL immunoglobulin domains. Fab may refer to this region in isolation, or this region in the context of a full length antibody, antibody fragment or Fab fusion protein.

By "Fv" or "Fv fragment" or "Fv region" as used herein is meant a polypeptide that comprises the VL and VH domains of a single antibody. As will be appreciated by those in the art, these generally are made up of two chains in a Fab format and a single chain in the case of an scFv.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcqammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat. In some embodiments, as is more fully described below, amino acid modifications are made to the Fc region, for example to alter binding to one or more FcγR receptors or to the FcRn receptor.

By "heavy constant region" herein is meant the CH1-hinge-CH2-CH3 portion of an antibody. Useful embodiments include the heavy constant regions of human IgG1, IgG2 and IgG4.

By "position" as used herein is meant a location in the sequence of a protein. Positions may be numbered sequentially, or according to an established format, for example the EU index for antibody numbering.

By "variable region" as used herein is meant the region of an immunoglobulin that comprises one or more Ig domains substantially encoded by any of the Vκ, Vλ, and/or VH genes that make up the kappa, lambda, and heavy chain immunoglobulin genetic loci respectively.

By "wild type or WT" herein is meant an amino acid sequence or a nucleotide sequence that is found in nature, including allelic variations. A WT protein has an amino acid sequence or a nucleotide sequence that has not been intentionally modified.

The BCE antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogeneous host cells.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about 10-4 M, at least about 10-5 M, at least about 10-6 M, at least about 10-7 M, at least about 10-8 M, at least about 10-9 M, alternatively at least about 10-10 M, at least about 10-11 M, at least about 10-12 M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore assay.

Antibodies

The present invention relates to the generation of BCE bispecific antibodies that bind two different antigens and are generally therapeutic antibodies. As is discussed below, the term "antibody" is used generally. Antibodies that find use in the present invention can take on a number of formats as described herein, including traditional antibodies as well as antibody derivatives, fragments and mimetics, described herein.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to the IgG class, which has several subclasses, including, but not limited to IgG1, IgG2, IgG3, and IgG4. It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

A useful comparison of CDR numbering is as below, see Lafranc et al., Dev. Comp. Immunol. 27(1):55-77 (2003):

TABLE 1

|  | Kabat + Chothia | IMGT | Kabat | AbM | Chothia | Contact |
|---|---|---|---|---|---|---|
| vhCDR1 | 26-35 | 27-38 | 31-35 | 26-35 | 26-32 | 30-35 |
| vhCDR2 | 50-65 | 56-65 | 50-65 | 50-58 | 52-56 | 47-58 |
| vhCDR3 | 95-102 | 105-117 | 95-102 | 95-102 | 95-102 | 93-101 |
| vlCDR1 | 24-34 | 27-38 | 24-34 | 24-34 | 24-34 | 30-36 |
| vlCDR2 | 50-56 | 56-65 | 50-56 | 50-56 | 50-56 | 46-55 |
| vlCDR3 | 89-97 | 105-117 | 89-97 | 89-97 | 89-97 | 89-96 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The CDRs contribute to the formation of the antigen-binding, or more specifically, epitope binding site of antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning."

By "functionally silent epitope" in the context of the invention means that the binding of an antibody, including the BCE antibodies of the invention, to a functionally silent epitope on a receptor protein does not significantly alter the biologic function of the protein. In preferred embodiments, the functionally silent epitope is sufficiently sterically placed such that the binding of an antibody to the silent epitope does not block the active site, e.g. the ligand for the active site can still be bound. In some cases, as will be appreciated by those in the art, a receptor protein may have more than one biological functions and/or more than one active site, e.g. different ligands may bind for different functionalities of the receptor protein. In that case, a functionally silent epitope is defined by the active site of particular interest in the system of interest. In general, a functionally silent epitope means that the activity of the target protein is substantially similar in the presence or absence of the antibody, wherein the activity in the presence of the antibody is from 80-100% of the activity in the absence of the antibody.

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest in the present invention are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

The light chain generally comprises two domains, the variable light domain (containing the light chain CDRs and together with the variable heavy domains forming the Fv region), and a constant light chain region (often referred to as CL).

Another region of interest for additional substitutions, outlined below, is the Fc region.

Thus, the present invention provides different antibody domains. As described herein and known in the art, the heterodimeric antibodies of the invention comprise different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, FAb domains and scFv domains.

By "bispecific antibody" herein is meant an antibody that binds two different antigens. As will be appreciated by those in the art, bispecific antibodies can have different valencies, as well. That is, a bispecific antibody can be bispecific and bivalent, meaning each antigen is bound by a single Fv, as shown in FIGS. 7A and D. Alternatively, a bispecific antibody can be bispecific and tetravalent, as shown in FIGS. 7B and C.

Figure 1:
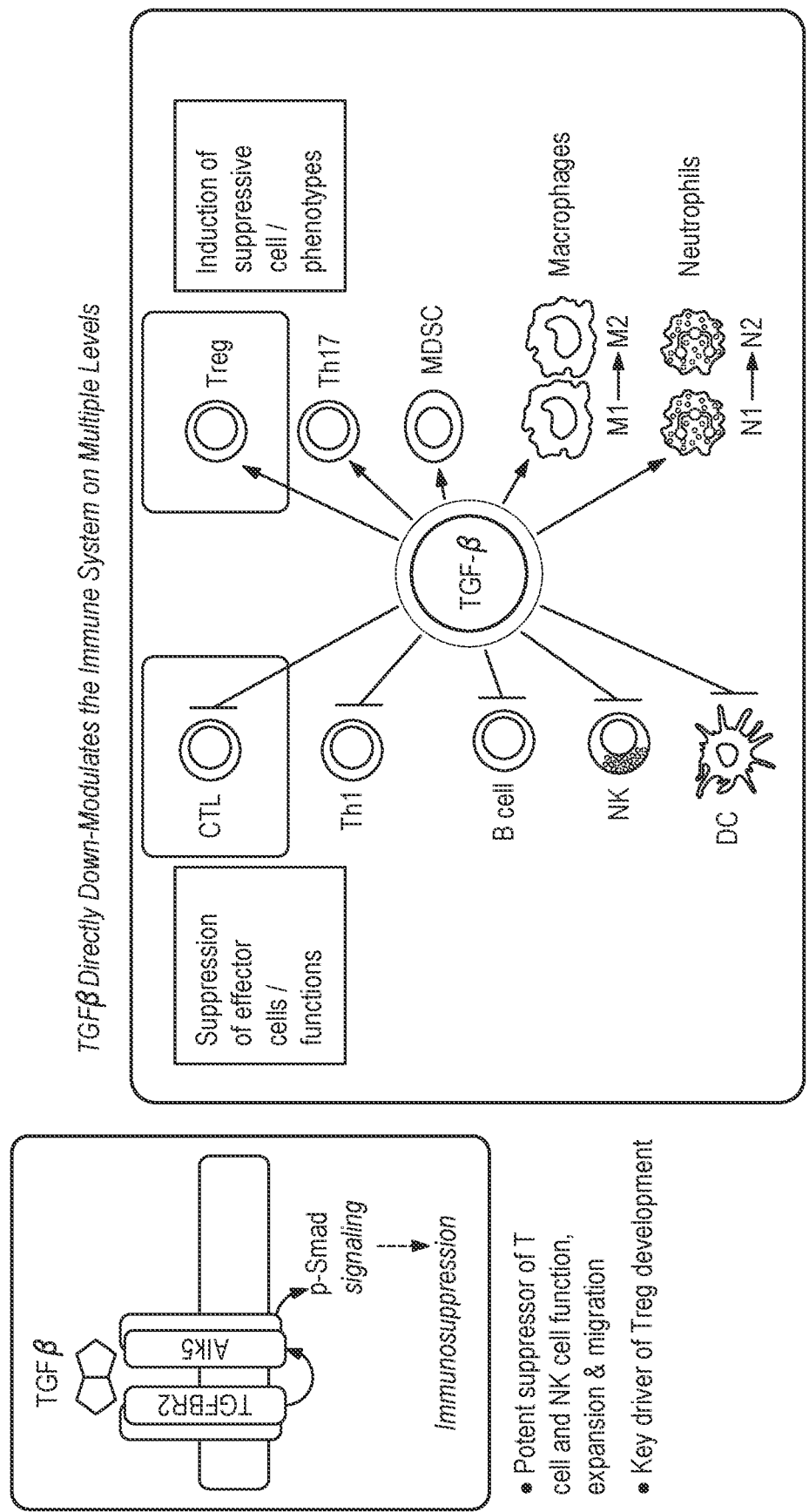
FIG. 1 depicts TGFβ biology, including its action on a number of different cell types, as well as the immunosuppresive pathway utilizing TGFBR2 and Alk5.
Figure 2:
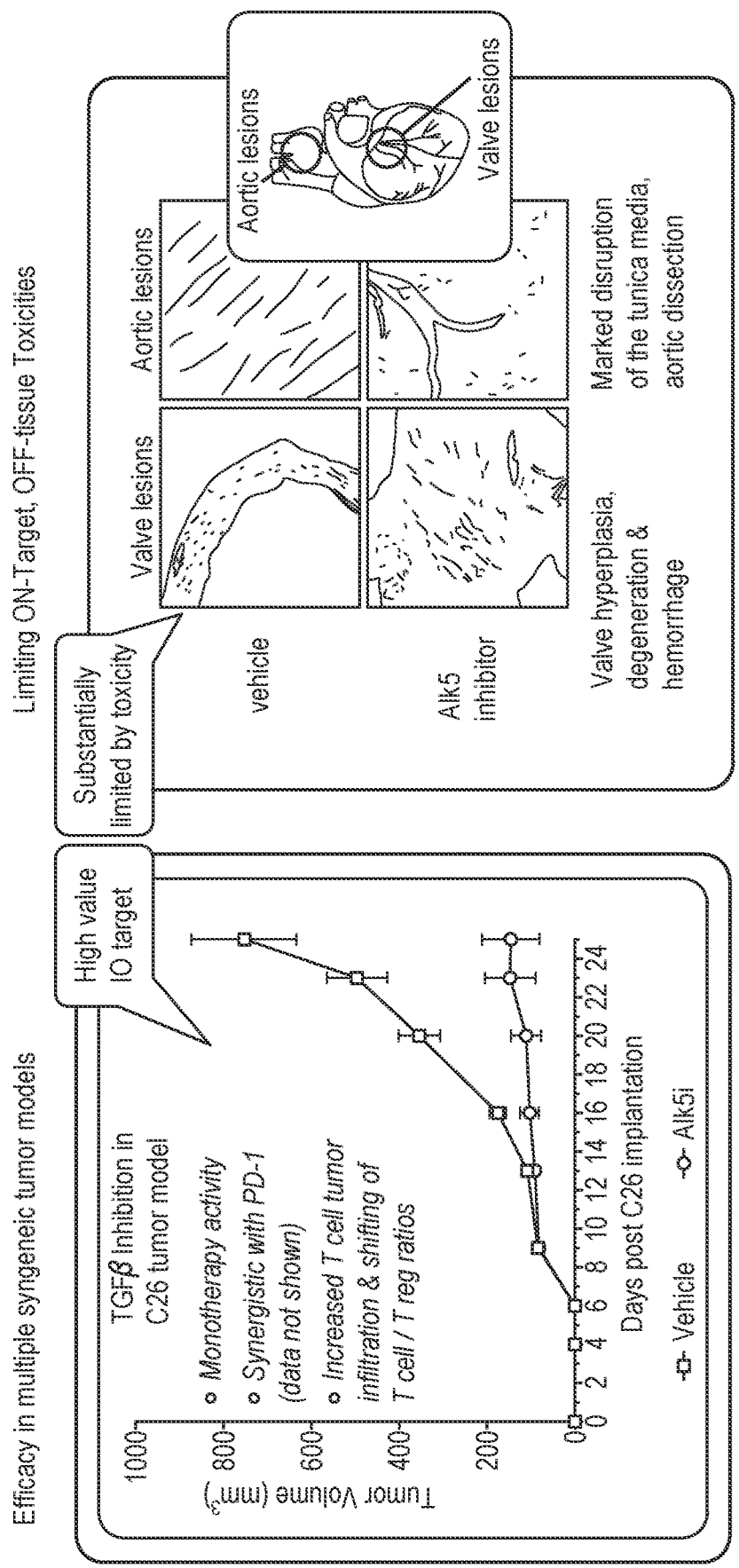
FIG. 2 shows that TGFβ inhibitors, such as monoclonal, monospecific antibodies, while showing significant efficacy, also results in significant toxic side effects, such as valve and aortic lesions. See for example Anderton et al., Toxicol.

There are a number of suitable bispecific formats for use in the present invention, including those in U.S. Pat. No. 9,358,286, US Publication 2014/0288275 and WO2014/145806, as well as those depicted and discussed in Kontermann, mAbs 4:2, 182-197 (2012) and Spiess et al., Mol. Immunol. 2015, doi.org/10.1016/j.molimm.2015.01.003, both of which are expressly incorporated by reference in their entirety, and specifically for the formats depicted in Kontermann, FIG. 2 and all references cited therein for these structures, and the formats depicted in FIG. 1 of Spiess and all references cited therein for these structures.

Note that generally these bispecific antibodies are named "anti-receptor×anti-Zipcode" (e.g. anti-gp-130×anti-PD-1"), or generally simplistically or for ease (and thus interchangeably) as "receptor×Zipcode", etc. for each pair; for example, "gp-130×PD-1". Note also that the order of recitation (receptor×Zipcode or Zipcode×receptor) is not determinative unless specifically stated.

Included within the definition of "bispecific antibody" are monospecific antibodies that have been functionalized to contain an additional Zipcode binding moiety, sometimes referred to herein as "bifunctional antibodies". That is, as shown in FIG. 13 and FIG. 14, the additional binding moiety is conjugated chemically to the antibody to provide the binding to the Zipcode protein. In this embodiment, the bispecific antibody is similar to an "antibody drug conjugate", or ADC, in that a "traditional" monoclonal antibody that is bivalent and monospecific can be conjugated with an additional functional moiety, in this case a moiety that will bind to the Zipcode protein. As is known in the art, there are a number of different ways to conjugate functional moieties to antibodies.

The bifunctional antibodies are generally described herein with the ABDs of the antibody binding to the functionally silent epitope of the cell surface receptor and the functionalized moiety as binding to the Zipcode target protein, although this can be reversed as needed.

B. Introduction

The present invention is directed to a method of reducing the toxicity and side effects of antibody treatments directed to important signaling proteins such as TGFβ. TGFβ is an important and potent inhibitor of the immune system, as it directly down modulates the immune system on multiple levels, as is shown in FIG. 1. However, treatment with anti-TGFβ antibodies can lead to significant toxicities due to the presence of TGFβ on many cell types and tissues, and its importance in a number of receptor signaling complexes. Thus, it is difficult to target TGFβ on a particular cell type for inhibition with standard monospecific antibodies as its presence on other cells, e.g. non-target cells, leads to toxicity of the non-target cells or tissues. For example, treatment with anti-TGFβ antibodies can lead to significant cardiac toxicities, including valve and aortic lesions, as is generally shown in FIG. 2.

Thus, the present invention is directed to bispecific antibodies that only result in biological function (e.g. suppression of TFGβ binding) under particular conditions, e.g. the presence of CD45 in, on or in the vicinity of the cell type of interest (a Treg cell and not a macrophage or neutrophil, for example). Thus, these antibodies are referred to herein as "bispecific conditionally effective" antibodies, or "BCE" antibodies, since they are only effective to reduce signaling under certain conditions, e.g. the presence of an additional antigen to which the BCE antibody binds. Thus, the BCE antibodies of the invention utilize a "zipcode" mechanism, whereby the antibody is targeted not only to the receptor protein (e.g. in the relevant receptor signaling complex (RSC) such as TGFβR2) but also to a target protein that is expressed by the cell type of interest, e.g. Tregs or CTL cells. Thus the "zipcode", defined by the target protein antigen, only leads to biological functioning, e.g. inhibition of the receptor, when the zipcode target protein is present on or near the cell as well. Thus, the BCE antibodies of the invention do not inhibit the receptor protein directly, as they do not bind to the active site of the receptor protein to prevent ligand binding. Rather, the BCE antibodies of the invention bind to an epitope outside of the active site of the receptor protein, such that receptor protein-ligand interactions are not inhibited and thus do not cause toxicities and side effects associated with ligand inhibition on non-target cells. (This is referred to herein as "functionally silent"). Instead, one antigen binding domain of the BCE antibodies of the invention binds to the receptor protein at an epitope outside of the active site of the protein and the other to a target protein that is present or overexpressed in the disease state. The BCE antibody binds to the cell surface receptor protein, and, if the Zipcode protein is also present, such as PD-1 or PD-L1 that can be overexpressed in certain cells, then the BCE antibody also binds to the Zipcode protein, which prevents the cell surface protein from signaling, resulting in inhibition of the receptor protein and the desired treatment, only in the relevant tissues.

As a result, the bispecific antibody is only active on the correct target cell, e.g. CD45-expressing immune cells that are relevant in the disease signaling mechanism, but not active against other cell types that express the receptor but for which inhibition is not desired.

The BCE antibody binding to the target protein can be either inhibitory or silent. That is, using the case of TGFBR2 and CD45, while it is required that the BCE antibody bind outside the TGFβ binding active site on TGFBR2, this is not the case for the CD45 binding. Accordingly, the antigen binding domain on CD45 (or any target protein) can be either within an active site of the target protein, such that the target protein is functionally inhibited, or not. For example, as is known in the art, CD45 has two active sites, D1 and D2, which are structurally defined (see Kashio et at, JBC, doi:10.1074/jbc.273.50.33856 and Kuban-Jankowska et at, doi.10.1371/journal.pone.0052495.g004, both of which are hereby incorporated by reference in their entirety). The BCE antibodies of the invention can either bind to epitopes that block one or both of these active sites, or to a functionally silent epitope.

It should be noted that in some embodiments, it may be desirable to have the BCE antibody bind to the Zipcode protein in a functionally silent way as well, similar to the receptor protein binding at an epitope outside of the active site of the receptor.

V. BISPECIFIC CONDITIONALLY EFFECTIVE ANTIBODIES

As will be appreciated by those in the art, there are a number of useful bispecific formats that find use in the present invention, with different combinations of receptor protein targets and Zipcode targets, as more fully described below.

A. Useful Bispecific Formats

As described in Kontermann and Carter, supra, there are a number of bispecific formats that find use in the present invention.

1. scFv-Fab Format

In one embodiment, a scFv-Fab format is used, as pictured in FIG. 7A. In this embodiment, one heavy chain of the antibody contains a single chain Fv ("scFv", as defined herein) and the other heavy chain is a "regular" Fab format, comprising a variable heavy chain and a light chain. The two chains are brought together by the use of amino acid variants in the constant regions (e.g. the Fc domain, the CH1 domain and/or the hinge region) that promote the formation of heterodimeric antibodies as is described more fully below.

There are several distinct advantages to this format. As is known in the art, antibody analogs relying on two scFv constructs often have stability and aggregation problems, which can be alleviated in the present invention by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.).

This format utilizes a first monomer comprising an scFv, comprising a variable heavy and a variable light domain, covalently attached using an scFv linker, where the scFv is covalently attached to the N-terminus of a first Fc domain usually through a domain linker (which can be exogeneous or endogeneous (e.g. all or part of the native hinge domain)). This is sometimes referred to as the "scFv-Fc monomer". As will be appreciated in the art, the scFv can be in either orientation, from N- to C-terminus, e.g. vh-scFv linker-vl or vl-scFv linker-vh. Thus, in general, the format comprises [vh1-scFv linker-vl1-[optional domain linker]-CH2-CH3] format or [vl1-scFv linker-vh1-[optional domain linker]-CH2-CH3], with in many cases the format utilizing all or most of the hinge to comprise [vh1-scFv linker-vl1[hinge]-CH2-CH3] format or [vl1-scFv linker-vh[hinge]-CH2-CH3]. The second monomer of this format is a heavy chain [vh2-CH1-hinge-CH2-CH3], and the composition further comprises a light chain (vl2-CL).

In this embodiment, the two monomers (or heavy chains) are brought together to form a heterodimeric antibody using a "knobs in holes" or "KIH" approach, referring to amino acid engineering that creates steric influences to favor heterodimeric formation and disfavor homodimeric formation can also optionally be used; this is sometimes referred to as "knobs and holes"; as described in Ridgway et al., Protein Engineering 9(7):617 (1996); Atwell et al., J. Mol. Biol. 1997 270:26; U.S. Pat. No. 8,216,805, US 2012/0149876, all of which are hereby incorporated by reference in their entirety In addition, as described in Merchant et al., Nature Biotech. 16:677 (1998), these "knobs and hole" mutations can be combined with disulfide bonds to skew formation to heterodimerization. Of use in the present invention are T366S/L368A/Y407V paired with T366W, as well as this variant with a bridging disulfide, T366S/L368A/Y407V/Y349C paired with T366W/S354C.

Other variants that can be used to form heterodimeric Fc/antibody molecules are outlined in PCT/US2014/0115489, WO2012/058768 and WO2013/063702, all of which are incorporated by reference specifically for the variants in the Fc domains that contribute to heterodimerization.

2. DVD-Ig Format

In some embodiments, the bispecific antibody is in a "Dual Variable Domain-Ig" or "DVD-Ig™" format (see FIG. 7C) such as is generally described in U.S. Pat. No. 7,612,181, hereby expressly incorporated by reference in its entirety, and in particular for the Figures and Legends therein. In the DVD-Ig format, the antibody is tetravalent and bispecific, and comprises 4 chains: two homodimeric heavy chains and two identical light chains. The heavy chains each have a VH1-(optional linker)-VH2-CH1-hinge-CH2-CH3 structure and the two light chains each have a VL1-optional linker-VL2-CL structure, with VH1 and VL1 forming a first ABD and the VH2 and VL2 forming a second ABD, where the first and second ABDs bind a receptor protein and a Zipcode protein.

3. FIT-Ig Format

In some embodiments, the bispecific antibodies are in a tetravalent, bispecific homodimeric format referred to as "Fabs In Tandem" or "FIT-Ig" format as generally depicted in FIG. 7B. In this embodiment, the FIT-Ig comprises three different monomers: a first heavy chain monomer compris-ing VL2-CL-[optional domain linker]-VH1-CH1-hinge-CH2-CH3, a second monomer comprising a VL1-CL domain and a third monomer comprising a VH2-CH1 domain. These three monomers assemble to form a tetramer comprising two of the heavy chain monomers and the two light chain monomers.

As discussed herein, the hinge region and/or the optional domain linker in the heavy chain monomer can be rigid or flexible.

4. Fab Format

In some embodiments, a bivalent bispecific format is made by making two different antibodies, each with different Fc domain amino acid substitutions, one to the cell surface receptor protein and one to the Zipcode target, followed by treating the antibodies under conditions whereby the homodimers disassociate and heterodimers are formed. This general format is shown in FIG. 7D.

B. Antigen Binding Domains

As will be appreciated by those in the art, there are a wide variety of possible antigen binding domains that can be used in the present invention. As discussed herein, the ABD to the cell surface receptor generally binds to a "functionally silent" epitope, e.g. it binds to the receptor but doesn't inhibit at least one biological function of the receptor. As will be appreciated herein, it is generally quite straightforward to find antibodies that bind and do not block the function of the target antigen (these actually are the antibodies that are rejected in other programs).

1. Zipcode Antigen Binding Domains

In general, ABDs to Zipcode proteins are easy to generate, again, as there is no requirement that the ABD confer any activity, e.g. no inhibition or activation is required, although using ABDs that do inhibit activity Finding ABDs that bind to Zipcode proteins is within the skill of the art.

In one embodiment, the Zipcode protein is CD45. ABDs to CD45 are known in the art, and can be generated using conventional techniques.

In one embodiment, the Zipcode protein is FAP. ABDs to FAP are known in the art. There are additional ZipCodes for fibrosis.

In one embodiment, the Zipcode protein is CD33. ABDs to CD33 are known in the art.

In one embodiment, the Zipcode protein is PD-L1. ABDs to PD-L1 are well known in the art and include the variable heavy and variable light domains from atezolizumab, Medimmune2.14H9 OPT, avelumab, Medarex 12A4, Medarex 3G10, Medarex 10A5, and others.

In one embodiment, the Zipcode protein is PD-1. ABDs to PD-1 are well known in the art, and include the variable heavy and variable light domains from pembrolizumab, nivolumab, pidilizumab, Pfizer MK-3475, Novartis/Dana Farber BAP049, Renenger H7798N, Medimmune h1H3 var 6, Tesarao TSF-042/APE2058, camrelizumab, Beigene 317-4B6, Beigene 326-4A3, Macrogenics mAb 7(1.2), Junmeng done 38, Junmeng done 39, Junmeng don 48, Wyeth PD1-17, Wyeth PD1-28, Wyeth PD1-33, Wyeth-PD1-35 and others.

In one embodiment, the Zipcode protein is LAYN. ABDs to LAYN are known in the art.

In one embodiment, the Zipcode protein is KCNMA1. ABDs to KCNMA1 are known in the art.

2. Receptor Protein Binding Domains

In general, ABDs to receptor proteins are easy to generate, again, as there is no requirement for activity and in fact, in the case of the receptor proteins, functionally silent antibodies are desired. Finding ABDs that bind to receptor proteins is within the skill of the art.

C. Preferred Embodiments

A number of preferred embodiments are depicted in FIG. 6.

In one embodiment, the BCE antibody binds the receptor protein transforming growth factor (TGF)-beta receptor 2 (TGFBR2) and the zipcode target protein CD45 for use in immuno-oncology applications, e.g. TGFβ-driven immunosuppression. As shown in FIG. 5, CD45 has desirable features for use in a BCE antibody for selective antagonism of TGFβ signaling in immune cells. This BCE antibody (referred to herein as "TGFBR2×CD45 BCE antibody") is useful as an immuno-oncology molecule for the treatment of cancers. It has the advantage of selectively targeting immune cells while avoiding cardiovascular and other pleiotropic toxicities to permit maximal inhibition.

In additional embodiments, the BCE antibody binds the receptor protein TGFBR2 and a zipcode target protein selected from the immune targets CD11b, CD11c, CD38, CD45, CD48, CD68, CD97, CD185, CD205, CD210b, CD257, CD274, CD277, CD305, CD317, CD319, CD328, CD352, CD354, CD357, CD361, CD122, CD158b2, CD158e, CD158f1, CD158h, CD158i, CD160, CD16a, CD16b, CD181, CD243, CD32, CD337, CD85i, CD86, CDw210a, Q13873, A1A5B4, P30459, Q9H228, Q92673, P05534, 095977, P26010, P03989, P43116, Q8TD46, Q8NC42, P25105, Q5QGZ9, P18465, Q96P31, Q6UWL2, P14222, Q9UNW8, Q9H1C0, Q8IYL9, Q96BF3, P07550, Q96E93, Q9HB89, Q9Y336, Q6ZQN7, Q6DN72 and P0C0L4.

In one embodiment, the BCE antibody binds the receptor protein TGFBR2 and the zipcode target protein fibroblast activation protein, FAP. FAP is found on activated stromal fibroblasts in >90% of cancers. This BCE antibody (referred to herein as "TGFBR2×FAP BCE antibody") is useful as an immuno-oncology molecule for the treatment of cancers, due to the TGFβ-driven fibroblast expansion and activation seen in certain cancers. It has the advantage of selectively targeting immune cells while avoiding cardiovascular and other pleiotropic toxicities to permit maximal inhibition.

In one embodiment, the BCE antibody binds the receptor protein TGFBR2 and the zipcode target protein selected from fibrotic targets include: FAP, Ep-CAM, E-Cadherin, PDGFr alpha, Vimentin, CD31 and CD34.

In some embodiments, the BCE antibody binds adipose targets including SL36A2, PAT2, P2RX5, Carbonic Anhydrase IV, PDGFr alpha, ADRB3, Asc-1, SLC7A10, TMEM26, GRK5, CD137, CD39, CD73, GPCR43, GPCR120, GPCR103b, CD10, CD304, CD325, CD112, CD144, CD163, CD169, CD23, CD322, CD34, CD344, CD62P, P00533, Q13641, Q9H6B4, P01891, Q9UGT4, 060487, Q687X5, P04004, P07585, P02763, P54289, P55290, Q5VUB5, 000592, Q13421, P05186, P54762, P21453, P25106, Q9H7M9, Q16620, Q16602, Q8N3J6, P30479, P10321, P16444, P25101, P20039, 075487, Q96AP7, Q8IWT1, Q8N126, Q9HBW9, Q8IZF2, P04229, P25929, Q86T13, P35414, Q92959, Q9NY15, Q9BX97, P08913, P30556, 060896, Q6ZMJ2, P55058, P12111, P02452, P08123, P02790, P35555, P12110, P00734, P28799, P27169, P12109, P13611, 075629, P51884, P08603, Q8N6C5, P02765, P01042, P55268, Q14314, O14638, Q13201, Q6UY14, P02760, Q14CZ8, P01011, P20851, P04275, Q14112, Q7Z7G0, A6NMZ7, P04114, P00488, P02788, P20774, P51888, Q13361, Q9BXN1, P04003 and Q12805.

In one embodiment, the BCE antibody binds the receptor protein Colony Stimulating Factor 2 Receptor Alpha Subunit GMCSFRα, also sometimes referred to as CSF2RA, and the zipcode target protein CD33. This BCE antibody (referred to herein as "GMCSFRα×CD33 BCE antibody) is useful as an immuno-oncology molecule for the treatment of cancers, as it avoids counterproductive inhibitor of GM-CSF signaling in other key immune cells such as dendritic cells (DCs).

In one embodiment, the BCE antibody binds the receptor protein GMCSFRα, also sometimes referred to as CSF2RA, and the zipcode target protein MDSC. This BCE antibody (referred to herein as "GMCSFRα×MDSC" BCE antibody) is useful as an immuno-oncology molecule for the treatment of cancers, as it avoids counterproductive inhibitor of GM-CSF signaling in other key immune cells such as dendritic cells (DCs).

In one embodiment the BCE antibody binds to the receptor protein Signal-regulatory protein alpha SIRPα and the zipcode target protein PD-L1, which is expressed on tumor associated macrophages. This BCE antibody (referred to herein as "SIRPα×PD-L1" BCE antibody) is useful as an immuno-oncology molecule for the treatment of cancer, by selectively targeting tumor infiltrated macrophages while avoiding dose-dependent anemia. Suitable Fv sequences for the PD-L1 side are those of Genentech's atezolizumab.

In one embodiment, the BCE antibody binds to the interleukin 2 receptor, IL2R and the zipcode target protein layilin, LAYN which is expressed on tumor infiltrating Tregs. This BCE antibody (referred to herein as "IL2R× LAYN" BCE antibody) is useful as an immuno-oncology molecule for the treatment of cancer, by selectively targeting tumor infiltrated Tregs (limit immune-related adverse events) while avoiding counterproductive inhibition of IL-2 signaling in other key immune cells (i.e. CD8 T cells).

In one embodiment, the BCE antibody binds to PD-1 and the zipcode target protein Potassium Calcium-Activated Channel Subfamily M Alpha 1 KCNMA1 which is expressed on tumor infiltrating Tregs. This BCE antibody (referred to herein as "PD-1×KCNMA1" BCE antibody) is useful as an immuno-oncology molecule for the treatment of cancer, by selectively targeting tumor infiltrated T cells while avoiding healthy organ resident lymphocytes (limit immune-related adverse events). Suitable Fv sequences for the anti-PD-1 antigen binding domain are those of Keytruda® and Opdivo®.

In one embodiment, the BCE antibody binds to gp130 and a Zipcode MDSC target selected from the group of CD11b, CCR2, CD45, CD80, VEGFR1, VEGFRII, CD1d, CD1d1, CD2, CD31, CD43, CD44, C5aRI, EMR1, F4/80, CD16, CD32, CD32a, CD32b, CD32b/c, CD32c, CD16a, Cd16b, Galectin-3, Cd54, IL-1 RI, IL-4r alpha, CD49d, Cd11a, Ly-6G, Ly-6c, Cd115, CD301a, CD301a/b, CD301b, PD-L1, Cd162, CD62L, CD33 and Transferrin receptor.

In one embodiment, the BCE antibody binds to IL-6R and a Zipcode MDSC target selected from CD11b, CCR2, CD45, CD80, VEGFR1, VEGFRII, CD1d, CD1d1, CD2, CD31, CD43, CD44, C5aRI, EMR1, F4/80, CD16, CD32, CD32a, CD32b, CD32b/c, CD32c, CD16a, Cd16b, Galectin-3, Cd54, IL-1 RI, IL-4r alpha, CD49d, Cd11a, Ly-6G, Ly-6c, Cd115, CD301a, CD301a/b, CD301b, PD-L1, Cd162, CD62L, CD33 and Transferrin receptor.

In one embodiment, the BCE antibody binds to oncostatin M receptor and a Zipcode MDSC target selected from CD11b, CCR2, CD45, CD80, VEGFR1, VEGFRII, CD1d, CD1d1, CD2, CD31, CD43, CD44, C5aRI, EMR1, F4/80, CD16, CD32, CD32a, CD32b, CD32b/c, CD32c, CD16a, Cd16b, Galectin-3, Cd54, IL-1 RI, IL-4r alpha, CD49d, Cd11a, Ly-6G, Ly-6c, Cd115, CD301a, CD301a/b, CD301b, PD-L1, Cd162, CD62L, CD33 and Transferrin receptor.

In one embodiment, the BCE antibody binds to IL-11R and a Zipcode MDSC target selected from CD11b, CCR2, CD45, CD80, VEGFR1, VEGFRII, CD1d, CD1d1, CD2, CD31, CD43, CD44, C5aRI, EMR1, F4/80, CD16, CD32, CD32a, CD32b, CD32b/c, CD32c, CD16a, Cd16b, Galectin-3, Cd54, IL-1 RI, IL-4r alpha, CD49d, Cd11a, Ly-6G, Ly-6c, Cd115, CD301a, CD301a/b, CD301b, PD-L1, Cd162, CD62L, CD33 and Transferrin receptor.

In one embodiment, the BCE antibody binds to GMCSF receptor and a Zipcode MDSC target selected from CD11b, CCR2, CD45, CD80, VEGFR1, VEGFRII, CD1d, CD1d1, CD2, CD31, CD43, CD44, C5aRI, EMR1, F4/80, CD16, CD32, CD32a, CD32b, CD32b/c, CD32c, CD16a, Cd16b, Galectin-3, Cd54, IL-1 RI, IL-4r alpha, CD49d, Cd11a, Ly-6G, Ly-6c, Cd115, CD301a, CD301a/b, CD301b, PD-L1, Cd162, CD62L, CD33 and Transferrin receptor.

In one embodiment, the BCE antibody binds to the oncostatin receptor and a Zipcode gastrointestinal target selected from CD31, CD90, ICAM and VCAM.

In one embodiment, the BCE antibody binds to the IL-1 receptor and a Zipcode gastrointestinal target selected from CD31, CD90, ICAM and VCAM.

In one embodiment, the BCE antibody binds to the IL-4 receptor and a Zipcode gastrointestinal target selected from CD31, CD90, ICAM and VCAM.

In one embodiment, the BCE antibody binds to the IL-31 receptor and a Zipcode gastrointestinal target selected from CD31, CD90, ICAM and VCAM.

In one embodiment, the BCE antibody binds to the IL-17 receptor and a Zipcode gastrointestinal target selected from CD31, CD90, ICAM and VCAM.

In one embodiment, the BCE antibody binds to the LT alpha/beta receptor and a Zipcode gastrointestinal target selected from CD31, CD90, ICAM and VCAM.

In one embodiment, the BCE antibody binds to the MHC I and a Zipcode pancreatic target selected from GPR17, SSTR5, GPR37L1, TEX28, DRD3, DRD4, Insulin receptor, IGF-1r, GLP-1r, alpha-2 adrenergic receptor, Glut-1, Glut-2, NTSR2, GPR40, TMEM27, P2RY10, BACE-1, BACE-2, ADAM10, Sulfonyl urea receptor 1, NCLN, SLC30A3, SLC6A7 SLC4A3, EphA, ZP2, F2RL3, and GPR3.

VI. NUCLEIC ACIDS

The invention further provides nucleic acid compositions encoding the BCE antibodies of the invention. As will be appreciated by those in the art, the nucleic acid compositions will depend on the format and scaffold of the bispecific antibody. As discussed herein, there are a number of suitable bispecific antibody formats that find use in the present invention (see Kontermann and Speiss, discussed above). In some cases, there can be two, three or four protein sequences that comprise the bispecific antibody, depending on the format, and thus each protein chain is encoded by a nucleic acid sequence. Each nucleic acid sequence can be incorporated into a single expression vector or multiple expression vectors as needed.

As is known in the art, the nucleic acids encoding the components of the invention can be incorporated into expression vectors as is known in the art, and depending on the host cells used to produce the heterodimeric antibodies of the invention. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

In some embodiments, nucleic acids encoding each monomer and the optional nucleic acid encoding a light chain, as applicable depending on the format, are each contained within a single expression vector, generally under different or the same promoter controls. In embodiments of particular use in the present invention, each of these two or three nucleic acids is contained on a different expression vector.

The heterodimeric antibodies of the invention are made by culturing host cells comprising the expression vector(s) as is well known in the art. Once produced, traditional antibody purification steps are done, including an ion exchange chromatography step.

VII. FORMULATION OF BCE ANTIBODIES FOR IN VIVO ADMINISTRATION

Formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to provide antibodies with other specificities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

VIII. ADMINISTRATIVE MODALITIES

The antibodies and chemotherapeutic agents of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

An improvement in the disease may be characterized as a complete response. By "complete response" is intended an absence of clinically detectable disease with normalization of any previously abnormal radiographic studies, bone marrow, and cerebrospinal fluid (CSF) or abnormal monoclonal protein in the case of myeloma.

Such a response may persist for at least 4 to 8 weeks, or sometimes 6 to 8 weeks, following treatment according to the methods of the invention. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the bispecific antibodies used in the present invention depend on the disease or condition to be treated and may be determined by the persons skilled in the art.

An exemplary, non-limiting range for a therapeutically effective amount of an bispecific antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, the antibody is administered in a dose of 1 mg/kg or more, such as a dose of from 1 to 20 mg/kg, e.g. a dose of from 5 to 20 mg/kg, e.g. a dose of 8 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the bispecific antibody is administered by infusion in a weekly dosage of from 10 to 500 mg/kg such as of from 200 to 400 mg/kg Such administration may be repeated, e.g., 1 to 8 times, such as 3 to 5 times. The administration may be performed by continuous infusion over a period of from 2 to 24 hours, such as of from 2 to 12 hours.

In one embodiment, the bispecific antibody is administered by slow continuous infusion over a long period, such as more than 24 hours, if required to reduce side effects including toxicity.

In one embodiment the bispecific antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as of from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the bispecific antibody.

In a further embodiment, the bispecific antibody is administered once weekly for 2 to 12 weeks, such as for 3 to 10 weeks, such as for 4 to 8 weeks.

In one embodiment, the bispecific antibody is administered by maintenance therapy, such as, e.g., once a week for a period of 6 months or more.

In one embodiment, the bispecific antibody is administered by a regimen including one infusion of an bispecific antibody followed by an infusion of an bispecific antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In some embodiments the bispecific antibody molecule thereof is used in combination with one or more additional therapeutic agents, e.g. a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

IX. EXAMPLES

A. Example 1: Bispecific Antibody Co-Engagement of a PD-L1 ZipCode Protein and Gp130 Conditionally Inhibits IL-6 Activity The ability to selectively inhibit 130-mediated IL-6 signaling in PD-L1 ZipCode bearing cells with bispecific ZipCode antibodies were tested.

In this example, we generated gp130×PD-L1 bispecific antibodies in a human IgG1 background and tested the ability of PD-L1 to serve as an interfering ZipCode. HEK-293 cells naturally respond to IL-6 stimulation through gp130 activation of the JAK/Stat pathway, which can be readily measured by a SIE (sis-inducible element) luciferase reporter assay (Qiagen). The PD-L1 "ZipCode" (full length PD-L1 cDNA ORF, Origene) was introduced by transient transfection into HEK-293 cells and used for subsequent specificity testing.

Three different antibodies were tested. The first is a bispecific gp130×PD-1L1 antibody (Mab85) made using a first Fv to gp130 and a second Fv to PD-L1.

As shown in FIG. 8, reengineering a gp130 antibody (Mab-gp130) with a PD-L1 antibody (Tecentriq, MPDL3280A, or R05541267) as an asymmetric gp130×PD-L1 bispecific antibody (Mab-85) potently inhibited PD-L1 expressing HEK-293 cells [IC50: 3.03 nM] (FIG. 8A, solid gray line) with much greater selectivity than wild type HEK-293 cells [IC50: 200 nM estimated] (FIG. 8A, dashed black line). This is in dramatically contrast to conventional antagonist antibodies against gp130 that potently inhibit IL-6 responses [IC50: 8.6 nM] irrespective of "ZipCode" status (MAB 628, R&D systems) (FIG. 8B). A key consideration to generate the conditional activity of the gp130×PD-L1 antibody is the selection of a gp130 antibody that when tested individually is non-inhibitory or weakly/partially antagonistic, such as Mab-gp130 (FIG. 8C).

B. Example 2: Tandem Fab Bispecific Antibody Co-Engagement of a Pd-L1 Zipcode Protein and Gp130 Conditionally Inhibits IL-6 Activity In this example, we further tested the ability of PD-L1 to serve as an interfering ZipCode in the context a different bispecific format. In the previous example, we tested a bivalent asymmetric format where the resulting bispecific is monovalent per target and ZipCode, unlike normal antibodies that are typically bivalent per target. To engineer a bispecific that is tetravalent, or bivalent to both target and ZipCode, we used a Tandem Fab format in a human IgG1 background (FIG. 9). Similar to the previous example we found the subsequent tetravalent gp130×PD-L1 bispecific Zipcode antibody (Mab-50) potently and to a much more selectively inhibited PD-L1 ZipCode HEK-293 cells [IC50: 68 pM] (FIG. 9, solid gray line) than wild type HEK-293 cells (FIG. 9, dashed black line).

C. Example 3: Co-Engagement of PD-L1 Zipcode Protein and Gp130 is Achievable with Differing Human Fc Isotypes to Conditionally Inhibit IL-6 Activity In this example, we tested whether the ability of PD-L1 to serve as an interfering ZipCode was specific to a particular human Fc isotype. In the previous examples, we tested bispecific antibodies on a human IgG1 isotype background. IgG1 Fc is considered highly effective at effector recruitment, whereas IgG2 has considerably less effector function and often used in therapeutic circumstances where effector function is less desirable. As previously described we engineered gp130×PD-L1 ZipCode bispecific asymmetric bivalent (Mab-81) and a symmetric tetravalent Zipcode (Mab-58) antibodies, but this time on a human IgG2 backbone. Similar to previous results we found the bivalent ZipCode antibody (Mab-81) potently and more selectively inhibiting PD-L1 ZipCode HEK-293 cells [IC50: 146 pM] (FIG. 10A, solid gray line) than wild type HEK-293 cells (FIG. 10A, dashed black line). Also, the tetravalent ZipCode antibody (Mab-58) more selectively inhibited PD-L1 ZipCode HEK-293 cells [IC50: 74 pM] (FIG. 10B, solid gray line) compared to wild type HEK-293 cells (FIG. 10B, dashed black line)

D. Example 4: Co-Engagement of PD-L1 Zipcode Protein and Gp130 can be Improved Through Alterations of Antibody Fc Hinge Flexibility to Conditionally Inhibit IL-6 Activity In this example, we tested whether the ability and efficiency of PD-L1 to serve as an interfering ZipCode could be influenced by human Fc hinge flexibility. In general hinge flexibility may influence therapeutic potential and sometimes specific activities of many antibodies. As recombinant reformatting allows additional degrees of therapeutic assessment, hinge engineering is often incorporated into therapeutic protein engineering. In the first instance we compared the potencies of bivalent gp130×PD-L1 bispecific with a more flexible IgG1 hinge (Mab-85) to one with a more rigid hinge (Mab-81). In this case the bivalent composition with the more rigid IgG2 hinge was a more potent inhibitor [IC50: 146 pM vs 3.3 nM] (FIG. 11A). In the second instance we compared the potencies of tetravalent gp130×PD-L1 bispecific with a more flexible IgG1 hinge (Mab-50) to one with a more rigid hinge (Mab-58). In this format, IgG1 and IgG2 hinge selection did not substantially alter tetravalent ZipCode antibody potencies [IC50: 68 pM vs 74 pM] (FIG. 11B).

E. Example 5: Bispecific Antibody Co-Engagement of Different Types of Zipcode Proteins and Gp130 Conditionally Inhibits IL-6 Activity In this example, we tested whether other cell surface receptors could to serve as an interfering ZipCode. Here we tested TGFbR2 and TIGIT for their abilities to serve as interfering Zipcode proteins to gp130-mediated IL-6 signaling. Similar to previous examples, we created bispecific ZipCode antibodies reformatting gp130 combined with either TGFbR2 or TIGIT binding domains, followed by subsequent testing on HEK-293 cells that were transiently transfected with these corresponding ZipCode receptors and tested as before for IL-6 inhibition. Similar to previous results, we found the bivalent gp130×TGFbR2 ZipCode antibody (Mab-105) potently inhibited TGFbR2 ZipCode HEK-293 cells [IC50: 91 pM] (FIG. 12A, solid gray line) significantly better than wild type HEK-293 cells (FIG. 12A, dashed black line). Also, the tetravalent ZipCode antibody (Mab-62) selectively inhibited TIGIT ZipCode HEK-293 cells [IC50: 112 pM] (FIG. 12B, solid gray line) better than wild type HEK-293 cells (FIG. 12B, dashed black line).

F. Example 6: Antibody Conjugates can Co-Engage PD-L1 Zipcode Protein and Gp130 to Conditionally Inhibit IL-6 Activity In this example we tested whether the ability of cell surface proteins to serve as an interfering ZipCodes was restricted only to protein-protein interactions or if it were possible to be mediated by nonpeptidic agents conjugated to antibodies. Specifically, we tested whether an appropriate gp130 antibody conjugate could co-engage gp130 through the antibody variable region and PD-L1 via covalent antibody conjugate. SNAP tag is an engineered form of human $O^6$-alkylguanine-DNA alkyltransferase that specifically binds benzyl guanidine. In this case, we created a PD-L1 ZipCode and SNAP tag recombinant fusion (SNAP-PD-L1) to see whether co-engagement via gp130 through antibody variable domain binding, and SNAP-PD-L1 through the benzyl guanidine antibody conjugate binding, could collectively inhibit IL-6 activity selectively in SNAP-PD-L1 HEK-293 cells compared to wild type HEK-293 cells.

Similar to previous results with reformatted bispecific ZipCode antibodies, we found the ZipCode antibody conjugate (Mab-gp130-BG) specifically and potently inhibited SNAP-PD-L1 ZipCode HEK-293 cells [IC50: 43 pM] (FIG. 13, solid line) better than wild type HEK-293 cells (FIG. 13, dashed line).

G. Example 7: Bispecific Antibody Co-Engagement of Different Types of Zipcode Proteins and Gp130 Conditionally Inhibits IL-6 Activity In this example, we tested whether a spectrum of cell surface receptors could to serve as interfering ZipCodes via ZipCode antibody conjugate co-engagement. Similar to the previous example, we employed the recombinant SNAP-fusion approach and produced numerous structurally and functionally diverse ZipCode-SNAP tag fusions for their ability to co-engage with gp130 to conditionally inhibit IL-6 in a ZipCode-dependent manner. In every instance we observed a highly specific and potent inhibition of IL-6 activity with Mab-gp130-BG that was ZipCode-dependent. In rank order of potency the most potent inhibition was achieved with SNAP-PD-1 [IC50: 30 pM] (FIG. 14, panel A), followed by SNAP-TGFbR2 [IC50: 37 pM] (FIG. 7, panel D), SNAP-TIGIT [IC50: 40 pM] (FIG. 14, panel B), SNAP-ACVR2B [IC50: 82 pM] (FIG. 7, panel C), and SNAP-CD4 [IC50: 188 pM] (FIG. 14, panel E).

H. Example 8: TGF-betaR2 Antibody Generation and Characterization

Mice were immunized with recombinant human TGF-betaR2 protein and after assessment of positive serology, hybridomas were generated, grown to sufficient quantities, and their supernatants tested by ELISA for specific binding to TGF-beta R2 and not control Fc protein (FIG. 15). Clones that were positively corroborated to specifically bind TGF-bR2 and not Fc control protein, were sequenced and their HC and LC positively identified. Following the sequencing we corresponding genes were synthesized and cloned into mammalian expression vectors for protein production purposes. The resulting expression plasmids were transiently transfected HEK293 cell (FreeStyle) for full length antibody production. Each protein construct was generated as a human chimera, containing the mouse heavy and light chain variable regions as recombinant fusions to respective human heavy and light chain constant regions. The resulting proteins were purified Protein A chromatography and reconstituted in PBS used for subsequent testing. Each of the individually produced antibodies were first tested by ELISA to confirm the binding characteristics of the original done. Next the antibodies were tested for their ability to compete ligand binding to their cognate recombinantly produced receptors, in an ELISA-like format.

I. Example 9: TGF-Beta In Vitro Testing—Cell Line and Engineered Assays. SRE-SEAP Following corroborative binding testing and ligand competition each of the antibodies were tested for their ability to inhibit TGF-beta cell-based signaling. For quantitative measurements we used HEK293 cells stably transfected with a secreted alkaline phosphatase reporter under the control of smad responsive elements (SRE-SEAP reporter). The monospecific TGF-betaR2 antibodies are then tested for inhibition. Antibodies with highest affinity binding and weak or little competition are prioritized for bispecific ZipCode antibody production.

J. Example 10: ZipCode Antibody Generation and Characterization

Mice were immunized with either recombinant protein or DNA corresponding to the cDNA encoding region of the desired ZipCode ("Target", see "Target" lists) and after assessment of positive serology, hybridomas were generated, grown to sufficient quantities, and their supernatants tested by ELISA for specific binding to both human and mouse proteins. Clones that were positively corroborated to bind to their corresponding human and mouse ZipCodes were sequenced and their HC and LC positively identified. Following the sequencing we corresponding genes were synthesized and cloned into mammalian expression vectors for protein production purposes. The resulting expression plasmids were transiently transfected HEK293 cell (FreeStyle) for full length antibody production. Each protein construct was generated as a human chimera, containing the mouse heavy and light chain variable regions as recombinant fusions to respective human heavy and light chain constant regions. The resulting proteins were purified Protein A chromatography and reconstituted in PBS used for subsequent testing. Each of the individually produced antibodies were first tested by ELISA to confirm the binding characteristics of the original done. If appropriate the antibodies were tested for their ability to compete ligand binding to their cognate recombinantly produced receptors, in an ELISA-like format.

K. Example 11: Bispecific Antibody Production and In Vitro Testing with TGF-Beta Reporter Assay Bispecific ZipCode antibodies were produced in an asymmetric format whereby TGF-betaR2 and ZipCode ("target") are each engaged in a monovalent manner. Additionally, the bispecific ZipCode antibodies are also produced in a manner whereby TGF-betaR2 and ZipCode ("target") are each engaged in a bivalent manner. To test for ZipCode-dependent inhibition TGF-beta reporter cells are also stably transfected with respective collections of respective ZipCode proteins to test each of the corresponding ZipCode bispecific antibodies to determine ZipCoded-dependent inhibition and quantitative measures of potencies.

L. Example 12: In Vitro Testing—Primary Fibroblast Cell Line (Surrogate for Fibrosis-Specific ZipCode Antibody Identification.), as a Model for ZipCode Bioassay In this example, we tested whether primary FAP-positive fibroblast can be specifically targeted by bispecific ZipCode TGF-betaR2×FAP antibodies are capable of potently inhibiting TGF-beta signaling. Briefly, fibroblasts of human or mouse origin are treated to induce or maintain FAP expression and cultured in TC-plates that are suitable for TGF-beta bioassays. ZipCode antibodies and appropriate control antibodies are tested for the ability to inhibit TGF-beta signaling. A similar approach can be made using lymphocytes to test lymphocyte-specific TGF-betaR2 ZipCode antibodies, as well as adipocytes to test for adipose-specific TGF-betaR2 ZipCode antibodies.

M. Example 13: In Vivo Testing—PK-PD

Essentially, tissue specificity can be rapidly tested by systemic TGF-beta stimulation and assessment of tissues of interest compared to other TGF-beta responsive tissues to test whether the ZipCoded antibodies specifically inhibited TGF-beta signaling, as measured by increased pSmad3 in the tissues/organs of interest. This type of in vivo specific assessment may be facilitated by testing in the background of models of disease (induced or spontaneous). Categorically these would include normal control mice, fibrotic mice, and high fat diet mice, and numerous other candidate mice.

The invention claimed is:

1. A method of conditionally inhibiting a receptor signaling complex (RSC) comprising a receptor protein and a receptor ligand in a target cell comprising:

a) providing a cell capable of forming said receptor signaling complex, wherein said receptor protein binds said ligand at an active site;
b) contacting said cell with a bispecific antibody comprising:
   i) a first antigen binding domain that binds to said receptor protein at a first epitope outside of said active site;
   ii) a second antigen binding domain that binds to a target protein;
c) wherein if said cell expresses said target protein, said first antigen binding domain binds to said receptor protein and said second antigen binding domain binds to said target protein, thereby inhibiting the binding of said receptor protein and said ligand to reduce signaling; and
d) wherein if said cell does not express said target protein, said first antigen binding domain binds to said receptor protein and does not prevent binding of said ligand to said receptor protein to achieve receptor signaling, and
e) and wherein said receptor protein/target protein pair is selected from the group consisting of Type II Receptor for TGFβ (TGFBR2)/CD45, TGFBR2/Fibroblast Activation Protein (FAP), TGFBR2/Beta-3 Adrenergic Receptor (ADRB3), Colony Stimulating Factor 2 Receptor Alpha Subunit (GMCSFRα)/CD33, Signal-Regulatory Protein Alpha (SIRPα)/Programmed death-ligand 1 (PD-L1), Interleukin 2 Receptor (IL2R)/Layilin (LAYN), Program cell death protein 1 (PD-1)/Potassium Calcium-Activated Channel Subfamily M Alpha 1 (KCNMA1) and Glycoprotein 130 (gp130)/PD-L1.

* * * * *